United States Patent [19]

Shaked et al.

[11] Patent Number: 5,183,746

[45] Date of Patent: Feb. 2, 1993

[54] FORMULATION PROCESSES FOR PHARMACEUTICAL COMPOSITIONS OF RECOMBINANT BETA-INTERFERON

[75] Inventors: Ze'Ev Shaked, Berkeley; Tracy Stewart; Susan Hershenson, both of San Francisco; James W. Thomson, Albany; Terrance Taforo, San Leandro; Jody Thomson, Albany, all of Calif.

[73] Assignee: Schering Aktiengesellschaft, Berlin and Bergkamen, Fed. Rep. of Germany

[21] Appl. No.: 100,679

[22] Filed: Sep. 29, 1987

Related U.S. Application Data

[63] Continuation-in-part of Ser. No. 923,423, Oct. 27, 1986, abandoned.

[51] Int. Cl.⁵ .................. A61K 37/66; C07K 3/28
[52] U.S. Cl. ..................... 435/69.51; 424/85.6; 530/351
[58] Field of Search ........... 424/85, 85.6; 530/351; 435/68, 69.51

[56] References Cited

U.S. PATENT DOCUMENTS

| | | | |
|---|---|---|---|
| 4,343,735 | 8/1982 | Menge et al. | 260/112 R |
| 4,450,103 | 5/1984 | Konrad et al. | 260/112 R |
| 4,457,916 | 7/1984 | Hayashi et al. | 424/101 |
| 4,460,574 | 7/1984 | Yabrov | 424/85 |
| 4,507,281 | 3/1985 | Asculai et al. | 424/85 |
| 4,604,377 | 8/1986 | Fernandes et al. | |
| 4,606,917 | 8/1986 | Eppstein | |
| 4,647,454 | 3/1987 | Cymbalista | 424/80 |
| 4,675,164 | 6/1987 | Hasegawa et al. | |
| 4,675,184 | 6/1987 | Hasegawa et al. | 424/85 |
| 4,680,175 | 7/1987 | Estis et al. | |

FOREIGN PATENT DOCUMENTS

| | | |
|---|---|---|
| 897,276 | 3/1983 | Belgium . |
| 080879 | 6/1983 | European Pat. Off. . |
| 92918 | 11/1983 | European Pat. Off. . |
| 107498 | 5/1984 | European Pat. Off. . |
| 0128009 | 12/1984 | European Pat. Off. . |
| 0135171 | 3/1985 | European Pat. Off. . |
| 85400189.8 | 5/1985 | European Pat. Off. . |
| 150067 | 7/1985 | European Pat. Off. . |
| 0163111 | 12/1985 | European Pat. Off. . |
| 0168008 | 1/1986 | European Pat. Off. . |
| 133767 | 3/1986 | European Pat. Off. . |
| 86307070.2 | 9/1986 | European Pat. Off. . |
| 196203 | 10/1986 | European Pat. Off. . |
| 87104766.8 | 3/1987 | European Pat. Off. . |
| 231132 | 8/1987 | European Pat. Off. . |
| 87115693.1 | 10/1987 | European Pat. Off. . |
| 257890 | 3/1988 | European Pat. Off. . |
| 3325223 | 1/1985 | Fed. Rep. of Germany . |
| 59-10524 | 1/1984 | Japan . |
| 2160528 | 12/1985 | United Kingdom . |
| WO89/05158 | 6/1989 | World Int. Prop. O. . |
| WO89/02750 | 4/1990 | World Int. Prop. O. . |

OTHER PUBLICATIONS

Stedman's Medical Dictionary, 24th Ed., Williams & Wilkins, Baltimore, Md., p. 1031 (1982).
New Riverside University Dicitonary, The Riverside Publishing Company, Boston, Mass., p. 854 (1984).
Chem. Abs., 94:312 (1981) No. 20423j.
Japanese Laid-Open Patent Application No. 61-293926.
German Disclosure Specification No. DE 3308-458A.
Chem. Abs., 106:373 (1987) No. 107907k.

Primary Examiner—David L. Lacey
Assistant Examiner—Shelly J. Guest
Attorney, Agent, or Firm—Millen, White, Zelano and Branigan

[57] ABSTRACT

Stable pharmaceutical compositions suitable for parenteral administration to animals or humans are prepared comprising a therapeutically effective amount of a recombinant IFN-β protein dissolved in an inert carrier medium comprising as solubilizer/stabilizer(s) one or more biocompatible non-ionic polymeric detergents or a combination of one or more biocompatible non-ionic polymeric detergents with an additional solubilizing and/or stabilizing agent, such as sodium dodecyl sulfate or glycerol. The compositions are in liquid form or lyophilized.

7 Claims, 4 Drawing Sheets

FORMULATION PROCESSES FOR PHARMACEUTICAL COMPOSITIONS OF RECOMBINANT BETA-INTERFERON

This application is a continuation-in-part of U.S. Ser. No. 923,423 filed Oct. 27, 1986, now abandoned.

FIELD OF THE INVENTION

This invention is in the field of biochemical engineering. More particularly, the invention concerns improved pharmaceutical compositions of biologically active recombinant beta-interferon (IFN-$\beta$) protein which is suitable for therapeutic administration to humans. Further, the invention concerns an improved process for preparing and formulating such IFN-$\beta$ compositions.

BACKGROUND OF THE INVENTION

Naturally occurring interferons (IFNs) are species-specific proteins, often glycoproteins, produced by various cells upon induction with viruses, double stranded RNAs, other polynucleotides, antigens and mitogens. Interferons exhibit multiple biological activities such as antiviral, antiproliferative, immunomodulatory, and anticellular functions. At least three distinct types of human interferons have been identified and characterized in terms of their anti-viral, anti-growth and activation of natural killer cell (NK) activities. They are produced by leukocytes, lymphocytes, fibroblasts and the immune system and are classified as $\alpha$, $\beta$ and $\gamma$ interferons. These are reported to be different proteins coded for by distinct structural genes.

Native human $\beta$-interferon (HuIFN-$\beta$) is generally produced by superinducing human fibroblast cultures with poly-IC (polyriboinosinic acid and polyribocytidylic acid) and isolating and purifying the HuIFN-$\beta$ thus produced by chromatographic and electrophoretic techniques. Proteins or polypeptides which exhibit native $\beta$-interferon activity may also be produced using recombinant DNA technology by extracting poly-A-rich 12S messenger RNA from virally induced human cells, synthesizing double-stranded c-DNA using the m-RNA as a template, introducing the c-DNA into an appropriate cloning vector, transforming suitable microorganisms with the vector, harvesting the bacteria and extracting the HIFN-$\beta$ therefrom. Nagola, S. et al., *Nature*, 284:316 (1980); Goeddel, D.V. et al., *Nature*, 287:411 (1980); Yelverton, E. et al., *Nuc. Acid Res.*, 9:731 (1981); Streuli, M. et al., *Proc. Nat'l. Acad. Sci.* (U.S.), 78:2848 (1981); European Pat. Application Numbers 28033, published May 6, 1981; 321134, published Jul. 15, 1981; 34307 published Aug. 26, 1981; and Belgian Patent 837397, issued Jul. 1, 1981 describe various currently used methods for the production of $\beta$-interferon employing recombinant DNA techniques. The expressed proteins or polypeptides have been purified and tested and have been found to exhibit properties similar to those of native IFNs. Bacterially produced IFNs thus appear to have potential therapeutic use as antiviral and anti-tumor agents and the production of IFNs by such bacterial fermentations is expected to yield sufficiently large quantities of IFN at a relatively low cost for clinical testing.

Further, HuIFN-$\beta$ genes have been altered by, for example, oligonucleotide-directed mutagenesis to produce IFN-$\beta$ protein analogs thereof, such as the human recombinant cysteine-depleted or cysteine-replaced interferon-B analogs (muteins) disclosed in U.S. Pat. No. 4,588,585 issued May 13, 1986 to Mark et al. Specifically disclosed in that patent is the recombinant IFN-$\beta$ mutein wherein the cysteine at latter IFN-$\beta$ mutein is IFN-$\beta_{ser17}$.

Procedures for recovering and purifying bacterially produced IFNs are described in U.S. Pat. Nos. 4,450,103; 4,315,852; 4,343,735; and 4,343,736; and Derynck et al., *Nature* (1980) 287:193-197 and Scandella and Kornberg, *Biochemistry*. 10:4447 (1971). Generally with these methods the IFN is not produced in a sufficiently pure form and in sufficiently large quantities for clinical and therapeutic purposes and the resulting IFN preparations produced by recombinant DNA techniques have residual amounts of chemicals, such as sodium dodecyl sulfate (SDS) and other surfactants or precipitants used in the extraction and purification steps.

*E. coli* expressed recombinant IFN-$\beta$ and analogs thereof are insoluble in solutions which are at a pH range of 6 to 9. Therefore, various processes and additives have been devised to solubilize these proteins. Several methods currently available for the preparation, recovery and purification of bacterially produced proteins are listed immediately below.

U.S. Pat. No. 4,315,852 to Leibowitz et al. describes a method for the acid extraction of leukocyte interferon from bacterial cells and neutralization of the extractant to obtain the interferon.

U.S. Pat. No. 4,343,735 to Menge et al. teaches a process for the purification of interferon by partitioning it in an aqueous multi-phase system in the presence of ion exchangers which are soluble in the system and are derivatives of polyethers.

U.S. Pat. No. 4,343,736 to Uemura et al. discloses a method for recovering interferon by absorption of water-insolubilized heparin and then eluting the interferon with an aqueous solution of an inorganic salt and chondroitin sulfate.

U.S. Pat. No. 4,289,689 to Friesen et al. discloses how to recover and purify human native $\beta$-interferon by use of affinity chromatography and high pressure liquid chromatography.

U.S. Pat. No. 4,364,863 to Leibowitz et al. describes a method of extracting fibroblast interferon from bacteria using a low pH followed by a high pH extraction procedure.

U.S. Pat. No. 4,450,103 to Konrad et al. discloses solubilizing the protein in an aqueous medium with an appropriate solubilizing agent, extracting the protein from the aqueous medium with 2-butanol or 2-methyl-2-butanol, and precipitating the protein from the alcohol phase.

U.S. Pat. No. 4,530,787 to Shaked et al. describes a process for oxidizing recombinant proteins such as IFN-$\beta$ selectively and stoichiometrically using o-iodosobenzoic acid to ensure that the protein will be functionally equivalent to its native counterpart.

Many heterologous proteins are precipitated intracellularly in the form of refractile or inclusion bodies which appear as bright spots visible within the enclosure of the cell under a phase contrast microscope at magnifications down to 1000 fold. See e.g., Miller et al., *Science* (1982) 215:687-690; Cheng, *Biochem. Biophys. Res. Comm.*, (1983) 111:104-111; Becker et al., *Biotech. Advs.* (1983) 1:247-261; Kleid et al., ch. 25 in *Developments in Industrial Microbiology*, Vol. 25, p. 317-325 (Society for Industrial Microbiology, Arlington, Va., 1984); Marston et al., *Bio/Technology.* (September, 1984), pp. 800–804.

Purification and activity assurance of precipitated heterologous proteins is also described by U.S. Pat. Nos. 4,511,502; 4,511,503; 4,512,922; 4,599,127 and 4,518,526; and EP 114,506.

Commonly owned U.S. application Ser. Nos. 749,951 filed Jun. 26, 1985 now abandoned and U.S. Ser. No. 843,997, filed Mar. 25, 1986, now U.S. Pat. No. 4,748,234, both to Dorin et al., and entitled "Process for Recovering Refractile Bodies Containing Heterologous Proteins from Microbial Hosts" disclose improved methods for recovering and purifying refractile bodies. To isolate the refractile material, the processes initially involve disrupting the cell wall and membrane of the host cell, removing greater than 99% by weight of the salts from the disruptate, redisrupting the desalted disruptate, adding a material to the disruptate to create a density or viscosity gradient in the liquid within the disruptate, and separating the refractile material from the cellular debris by high-speed centrifugation. The heterologous protein, preferably recombinant IFN-$\beta$ or interleukin-2 (IL-2), is then extracted from the refractile bodies and solubilized with a denaturing agent such as sodium dodecyl sulfate (SDS). The SDS is later removed by a desalting column.

Wang et al., *J. Parenteral. Drug Assoc;* 34, 452–462 (1980) provides a review of excipients and pHs for parenteral products used in the United States. A list of solubilizing agents such as detergents and lipids in use for various drugs is provided in Table I thereof and under section 11 entitled "Solubilizers, Wetting Agents or Emulsifiers" of that table, polyethylene glycol 300, polysorbate 20, 40 and 80, and propylene glycol among others are listed for a variety of pharmaceuticals. Below are referenced some examples of interferon and related formulations.

U.S. Pat. No. 4,647,454 to Cymbalista et al. discloses a method of stabilizing human fibroblast interferon with polyvinyl pyrrolidone.

U.S. Pat. No. 4,460,574 to Yabrov discloses a pharmaceutical composition comprising native human $\alpha$- and $\beta$-interferons used for rectal or urogenital treatment of human interferon-sensitive diseases.

U.S. Pat. No. 4,462,940 to Hanisch et al. ('940 patent) discloses a process for formulating interferon by mixing the interferon and a protein stabilizer, such as normal serum albumin, at a pH of about 10.5 to 12.5 for 5 minutes and then adjusting the pH to 7.5 to obtain a soluble mixture. The '940 patent to Hanisch et al. further describes a method for recovering and purifying a lipophilic protein such as human recombinant interferon-$\beta$ or IL-2 which comprises solubilizing the protein into an aqueous medium with a suitable solubilizing agent, such as sodium dodecyl sulfate (SDS), extracting the solubilized protein with an aliphatic alcohol, precipitating the protein from the alcohol phase with an aqueous buffer, and diafiltering the protein at a pH of about 10.5 to 12.5 against water or against mixtures of water and aliphatic alcohols adjusted to a pH of about 10.5 to 12.5, to remove the solubilizing agent (SDS) or reduce its concentration.

One aspect of the instant invention concerns a process alternative to the method described above and claimed in U.S. Pat. No. 4,462,940. Said process alternative avoids the high pH range (pH 10.5 to 12.5) required to remove certain solubilizing agents such as SDS during diafiltration or desalting, preferably desalting.

Commonly owned, U.S. application Ser. No. 775,751, filed Sept. 13, 1985 now U.S. Pat. No. 4,992,271, entitled "An Improved Formulation for Lipophilic Proteins" outlines a high pH and a low pH process for recovering and purifying lipophilic recombinant proteins, such as human IFN-$\beta$ and interleukin-2, from host strains to yield a protein preparation which may be formulated into a stable pharmaceutical composition. Said composition carrying a therapeutically effective amount of the biologically active lipophilic protein dissolved in a non-toxic, inert, therapeutically compatible aqueous-based carrier medium at a pH of 6.8 to 7.8 also contains a stabilizer for the protein, such as human serum albumin, human serum albumin and dextrose, or human plasma protein fraction.

Commonly owned, U.S. application Ser. No. 780,551, filed Sept. 26, 1985, now U.S. Pat. No. 4,816,440, entitled "Stable Formulation of Biologically Active Proteins for Parenteral Injection," discloses pharmaceutical compositions containing IFN-$\beta$ or interleukin-2 dissolved in a stable carrier medium at pH 7.0 to 8.0 stabilized with sodium laurate.

Commonly owned, U.S. application Ser. Nos. 749,955, filed Jun 26, 1985, now abandoned and Ser. No. 866,459 filed May 21, 1986 (Katre et al.), now U.S. Pat. No. 4,766,106, disclose pharmaceutical compositions wherein recombinant IFN-$\beta$, IL-2 or an immunotoxin is dissolved in an aqueous carrier medium at pH 6 to 8 without the presence of a solubilizing agent. The protein is solubilized by selectively conjugating it via a coupling agent to a water-soluble polymer selected from polyethylene glycol homopolymers or polyoxyethylated polyols.

Japanese Laid-Open Patent Application (Kokai) No. 59-10524 (published Jan. 20, 1984) entitled "An Interferon Composition and a Method of Manufacturing the Same" discloses a micelle solution for rectal administration prepared by mixing (a) an unsaturated fatty acid, (b) a polyoxyethylene fatty acid ester, alkyl polyoxyethylene ether or sucrose fatty acid ester, (c) water and (d) interferon.

European Patent Application Publication No. 135,171 (published Mar. 27, 1985) discloses pseudomonophase, microemulsion compositions for topical application of interferons, preferably leukocyte interferon A. The compositions comprise a therapeutically effective amount of interferon, 30–70% by volume of a surface active agent having a hydrophilic-lipophilic balance (HLB) of from 12–15 and dual solubility in water/oil; 5–45% of a vegetable oil; and 5–45% water. The surface active agents disclosed therein are polyethylene glycol derivatives of castor oil composed on average of 25–36 moles of ethylene oxide per mole of castor oil. Such an oil-based microemulsion is not stable and is subject to phase separation.

U.S. Pat. No. 4,507,281 discloses compositions comprising about $10^4$ to $10^6$ I.U. of human leukocyte interferon, about 1% to 5% by weight of a non-ionic surface active agent having at least one ether or amide linkage, and a physiologically acceptable carrier. Such compositions are topically administered to treat herpes simplex infections wherein a therapeutic effect is attributed to such non-ionic surfactants in their ability to dissolve the lipid-containing envelope of the herpes simplex virus. The preferred non-ionic surfactants referred to therein include: nonylphenoxypolyethoxy ethanol (trade name Nonoxynol-9); p-diisobutylphenoxypolyethoxy ethanol (tradename Triton X-100); polyoxyethylene (10) oleyl ether (trade name Brij-97); and onyx-ol (trade name Onyx-ol 345). Such pharmaceutical compositions are preferably administered in lotion, cream, oil, or emulsion formulations. See also European Patent Application Publication No. 77,063 which is a foreign equivalent thereof.

There remains a need in the art for formulations of biologically active, recombinant beta-interferons that are pure enough for clinical administration but substantially or totally free of residual strong detergents, such as SDS, used in the extraction and purification processes. Further, there is a need for formulations that provide alternatives to those containing non-IFN-$\beta$ protein, such as those containing albumin.

Further, alternative formulation processes for such biologically active, recombinant beta-interferons which avoid very high pH ranges are desirable.

SUMMARY OF THE INVENTION

The present invention provides for stable pharmaceutical compositions of matter suitable for parenteral administration to animals or humans comprising a therapeutically effective amount of a recombinant interferon-$\beta$ protein dissolved in an inert carrier medium comprising as a solubilizer/stabilizer an effective amount of one or more biocompatible non-ionic polymeric detergents. Such compositions can further comprise an additional solubilizing or stabilizing agent, for example, sodium dodecyl sulfate (SDS) and glycerol.

The use of glycerol in combination with one or more non-ionic detergents of this invention allows for an order of magnitude decrease in the concentration range of the non-ionic detergents required to solubilize/stabilize the IFN-$\beta$.

The formulations of this invention can be in liquid form or lyophilized.

Another aspect of the invention is methods of screening for one or more biocompatible non-ionic polymeric detergents or for combinations of one or more of said detergents with another solubilizing or stabilizing agent capable of solubilizing and stabilizing pharmaceutical compositions of recombinant interferon-$\beta$ (IFN-$\beta$), comprising the steps of:

(a) passing extracted, purified IFN-$\beta$ in sodium dodecyl sulfate (SDS) on a desalting column equilibrated in sodium laurate in an elution buffer at pH 9.0–10.0 to form an eluate;

(b) lowering the pH of the eluate to about pH 2–3.3;

(c) centrifuging and filtering the eluate to remove the precipitated sodium laurate;

(d) adding to the filtrate an effective amount of one or more of said detergents or said combination of one or more of said detergents with another solubilizing or stabilizing agent; (e) adjusting the pH of the filtrate to 3.5 to 9.5; and (f) allowing said filtrate to stand for about 24 hours at pH 3.5 to 9.5.

The invention further provides for methods of preparing stable, pharmaceutical compositions of recombinant interferon-$\beta$ (IFN-$\beta$) protein wherein one such method comprises the steps of:

(a) extracting the IFN-$\beta$ from the disruptate of a host organism transformed to produce the protein;

(b) purifying the IFN-$\beta$ using as the last purification step a desalting step at a pH range of about 8.5 to 10 employing an elution buffer containing a fatty acid salt having a carbon chain containing from about 10 to about 12 carbons to form a desalted pool;

(c) lowering the pH of the desalted pool to a pH of about 2 to 4 thereby precipitating the fatty acid salt;

(d) removing the precipitated salt from the pool by centrifugation and filtration;

(e) adding to the desalted pool an effective amount of one or more non-ionic biocompatible polymeric detergents, or a combination of one or more biocompatible non-ionic polymeric detergents and another solubilizing or stabilizing agent, in effective amounts to stabilize and solubilize the IFN-$\beta$;

(f) adjusting the pH of the pool to a range of between 4.0 and 8.0;

(g) adding an effective amount of a bulking/stabilizing agent to the pool; and (h) lyophilizing the formulation.

Another such method comprises the steps of:

(a') isolating refractile bodies containing the IFN-$\beta$ from a host organism transformed to produce said IFN-$\beta$;

(b') solubilizing said refractile bodies by employing sodium laurate;

(c') extracting and purifying said IFN-$\beta$ from the solubilized refractile material employing sodium laurate as the primary solubilizing agent;

(d') lowering the pH of the purified IFN-$\beta$ to a pH from about 2 to about 4;

(e') centrifuging and filtering the purified IFN-$\beta$ solution to remove the sodium laurate precipitate to create an IFN-$\beta$ pool;

(f') desalting the IFN-$\beta$ pool at a pH from about 2 to 4;

(g') adding to the IFN-$\beta$ protein solution an effective amount of one or more non-ionic biocompatible polymeric detergents, or of a combination of a non-ionic biocompatible polymeric detergent and another solubilizing or stabilizing agent to stabilize and solubilize the IFN-$\beta$;

(h') adjusting the pH of the IFN-$\beta$ solution to a pH range of 3.5 to 9.5;

(i') adding to the solution an effective amount of a bulking/stabilizing agent; and (j') lyophilizing the formulation.

The invention still further concerns a method of extracting recombinant interferon-$\beta$ (IFN-$\beta$) from a bacterial host transformed to produce it and then purifying and formulating said IFN-$\beta$ comprising the steps of:

(a) growing the transformed bacterial hosts in an appropriate fermentation medium;

(b) concentrating the bacterial host in the fermentation medium;

(c) disrupting the cell wall and cell membrane of the bacterial host;

(d) removing greater than 99% by weight of the salts from said disruptate by diafiltration or centrifugation;

(e) redisrupting the desalted disruptate;

(f) adding a material to the disruptate to increase the density or viscosity of, or to create a density or viscosity gradient in, the liquid within the disruptate;

(g) separating the refractile material from the cellular debris by high-speed centrifugation;

(h) solubilizing the refractile material in an aqueous buffer containing a reducing agent;

(i) extracting the solubilized refractile material with 2-butanol or 2-methyl-2-butanol;

(j) isolating said refractile material from the extractant;

(k) solubilizing the resulting IFN-$\beta$ particle pellet with an aqueous solution of sodium dodecyl sulfate at an IFN-β to sodium dodecyl sulfate ratio of about 1:3 to form a solution;

(l) adjusting the pH of the solution to about 9.5 and reducing the solubilized IFN-β with dithiothreitol;

(m) purifying the reduced IFN-β by chromatography;

(n) oxidizing the IFN-β from step (m);

(o) further purifying the oxidized IFN-β by gel chromatography and collecting the eluate containing the purified IFN-β;

(p) desalting the purified IFN-β eluate in a desalting column equilibrated and run in sodium laurate at pH 9.0 to 9.8;

(q) lowering the pH of the eluate to pH 3.0;

(r) centrifuging and filtering the solution to remove the precipitate;

(s) adding to the filtrate an effective amount of one or more non-ionic biocompatible polymeric detergents or a combination of one or more of said detergents and another solubilizing or stabilizing agent to solubilize and stabilize the IFN-β;

(t) adjusting the pH of the solution to 4.0 to 9.5;

(u) adding an appropriate bulking/stabilizing agent in a concentration of from about 0.25% to about 10%; and (v) lyophilizing the IFN-β solution.

DETAILED DESCRIPTION OF THE PREFERRED EMBODIMENTS

Figure 1:
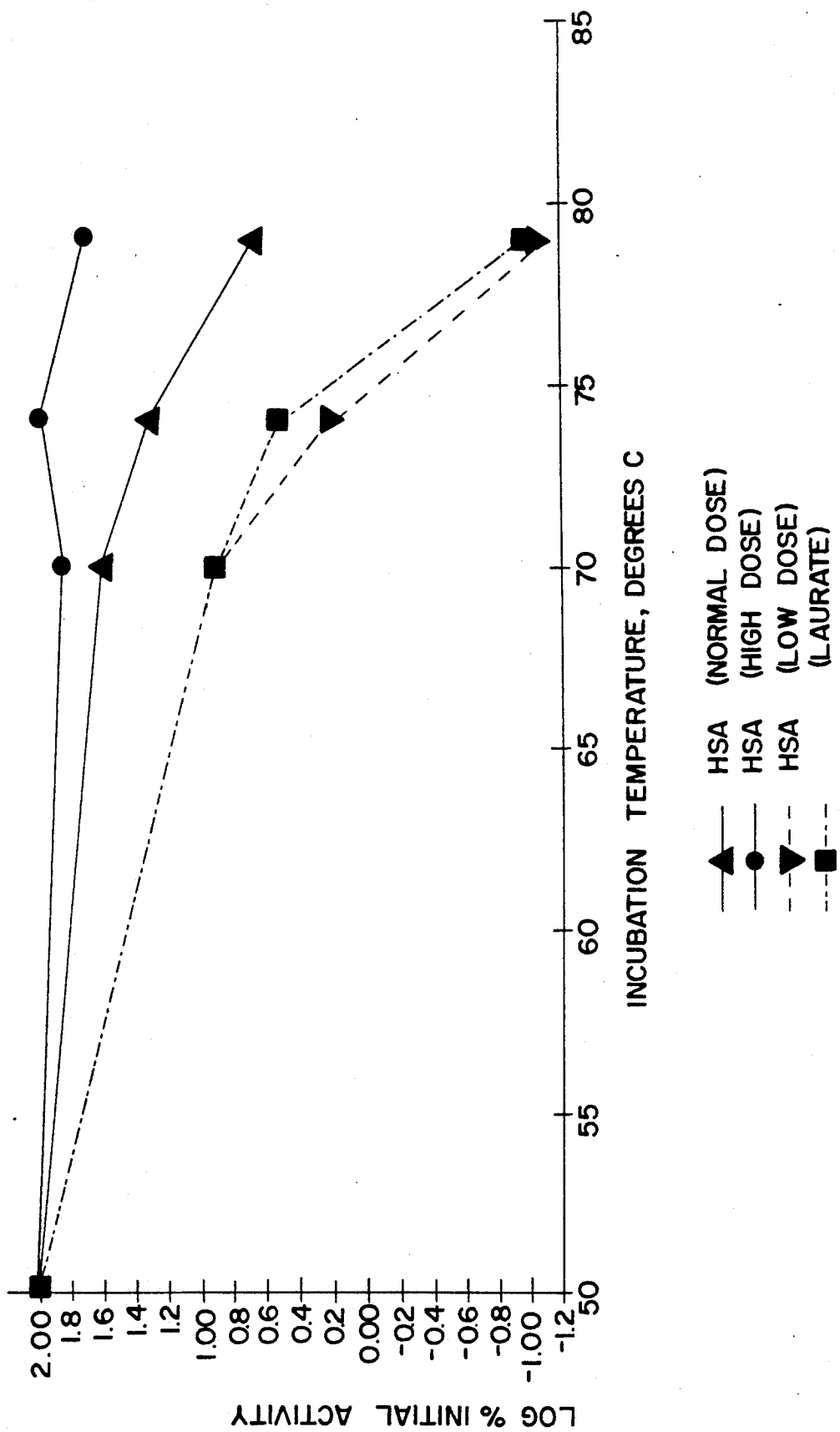
FIGS. 1-4 graphically illustrate linear non-isothermal stability (LNS) study results comparing representative formulations of this invention with sodium laurate and human serum albumin (HSA) IFN-β formulations. The HSA formulations are indicated in these figures as normal, high and low dose.

This invention provides for highly stable pharmaceutical compositions of matter suitable for parenteral administration to animals or humans comprising a therapeutically effective amount of a recombinant interferon-β protein dissolved in an inert carrier medium comprising one or more biocompatible non-ionic polymeric detergents or the combination of one or more non-ionic biocompatible polymeric detergents with an additional solubilizing/stabilizing agent.

The term "recombinant β-interferon," designated as IFN-β, preferably human IFN-β, refers to fibroblast interferon having biological activity comparable to native IFN-β, prepared by recombinant DNA techniques as described in the art. In general, the gene coding for interferon is excised from its native plasmid and inserted into a cloning vector to be cloned and then into an expression vector, which is used to transform a host organism, Preferably a microorganism, and most preferably $E.\ coli$. The host organism expresses the foreign interferon gene under certain conditions to produce IFN-β. More preferably, the IFN-β is a mutein as described in U.S. Pat. No. 4,588,585, in which the cysteine normally occurring at position 17 of the wild-type or native molecule has been replaced by a neutral amino acid, such as serine or alanine. Most preferably, the IFN-β mutein is IFN-$β_{ser17}$.

The precise chemical structure of the IFN-β protein will depend on a number of factors. As ionizable amino and carboxyl groups are present in the molecule, a particular IFN-β protein may be obtained as an acidic or basic salt, or in neutral form. All such preparations which retain their bioactivity when placed in suitable environmental conditions are included in the definition of IFN-β proteins herein. Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of IFN-β protein herein so long as the biological activity of the protein, as defined above, is not destroyed. It is expected, of course, that such modifications may quantitatively or qualitatively affect the activity, either by enhancing or diminishing the activity of the protein in the various assays.

Further, individual amino acid residues in the chain may be modified by oxidation, reduction, or other derivatization, and the protein may be cleaved to obtain fragments which retain activity. Such alterations which do not destroy biological activity do not remove the protein sequence from the definition.

The pharmaceutical compositions of this invention provide a means of maintaining recombinant IFN-β in soluble form and thereby stabilizing it in pH ranges wherein recombinant IFN-β is not readily soluble, by use of one or more solubilizes/stabilizers of this invention. Recombinant IFN-β, unlike native IFN-β, is considered to be lipophilic and hydrophobic, that is, insoluble or not readily soluble in water or an aqueous medium under ambient conditions of room temperature and atmospheric pressure at a pH of between about 5 and about 8. The most difficult IFN-β solubility problems are those that occur with nonglycosylated IFN-β produced by a transformed bacterial host, most notably $E.\ coli$. Therefore, the pharmaceutical compositions of this invention are especially useful in solubilizing/stabilizing nonglycosylated IFN-β produced in $E.\ coli$, and it is preferred that the recombinant IFN-β of the pharmaceutical o compositions of this invention be of such origin.

As used herein, the term "physiological pH" refers to a pH which is pharmaceutically acceptable to mammals. Neutral pH is herein considered to be a pH in the range of about 6.0 to about 8.5, preferably about 6.0 to about 8.0.

As used herein, the term "stabilizer/solubilizer" as applied to the recombinant IFN-β formulations refers to essentially non-toxic and non-immunogenic compositions which alone or in combination act not only to stabilize the IFN-β against denaturation and loss of biological activity, but also to solubilize the lipophilic protein in an aqueous medium so that the pharmaceutical formulation constitutes an aqueous solution of IFN-β protein at pH 3.5 to 9.5, preferably about 4 to about 8, more preferably about 5.5 to about 6.5, and still more preferably about pH 6, from which the protein will not precipitate. The stabilizer/solubilizer compositions of the invention are one or more biocompatible, non-ionic polymeric detergents, or combinations of one or more biocompatible, non-ionic polymeric detergents with another solubilizing and/or stabilizing agent.

The term "primary solubilizing agent" is defined herein to mean a solubilizing agent, preferably a detergent and/or chaotrope, which is used to solubilize the IFN-β from the refractile bodies in the abbreviated or expanded front-end processes of purifying IFN-β described infra. The primary solubilizing agent is preferably then relied upon to maintain the IFN-$\beta$ in solution throughout the purification process up to its removal, preferably by desalting, before formulating the purified IFN-$\beta$ with the non-ionic detergents according to this invention. For example, in the purification scheme illustrated by Schemes 1A and 1B, sodium laurate is the primary solubilizing agent, whereas sodium dodecyl sulfate (SDS) is the primary solubilizing agent in the process illustrated by Schemes 2A and 2B.

As used herein the term "transformed" in describing host microorganism cell cultures denotes a microorganism that has been genetically engineered to produce IFN-$\beta$ that possesses biological activity comparable to native IFN-$\beta$. Bacteria are preferred microorganisms for producing IFN-$\beta$. E. coli is particularly preferred.

"Chaotropic environment" refers to an environment in which proteins are denatured or changed from their ordinary conformations. Chaotropic environments may be engendered by the presence of suitable concentrations of chaotropic agents, as described below, or may be the result of heat or pH alterations. The resultant environments are capable of disrupting hydrogen bonding in the protein and altering the thermodynamics of the surroundings in such a way that alternate three-dimensional conformations are preferred in the chaotropic environment to those found in more physiologically compatible environments.

The term "chaotropic agent" refers to a compound or compounds which, in aqueous solution and in a suitable concentration, engender a chaotropic environment and are capable of denaturing IFN-$\beta$ Guanidine salts (e.g., the hydrochloride) and alkali metal thiocyanates (e.g., sodium thiocyanate) and urea at concentrations in the range of about 4 to 9M, preferably 6 to 9M, are examples of chaotropic environments that will dissolve and denature IFN-$\beta$.

"Reducing conditions" are those required to place or maintain the IFN-$\beta$ in reduced form with respect to the cysteine residues. These conditions can most simply be provided by use of a suitable reducing agent (especially a thiol-containing reducing agent), or if the IFN-$\beta$ is already reduced (e.g., in the cellular environment), exclusion of air and oxidation catalysts or reagents may suffice.

The biocompatible non-ionic polymeric detergents are essentially non-toxic surface active agents used in the food, pharmaceutical, and cosmetic industries and have molecular weights in the range of approximately 100 to 250,000, and more preferably from about 180 to about 200,000. The term "detergent" herein is broadly defined to include compounds or mixtures of compounds known to those skilled in the art as detergents, emulsifiers, solubilizers, surfactants and/or surface-active agents.

The biocompatible non-ionic polymeric detergents used as solubilizers/stabilizers in the formulations of this invention are characterized by their ability either alone or in combination with another non-ionic detergent or with another type of solubilizing/stabilizing agent, preferably sodium dodecyl sulfate (SDS) or glycerol, to solubilize IFN-$\beta$ at a pH range of from about 3.5 to about 9.5, from about 5 to about 8.

The ampiphilic of non-ionic detergents is often expressed in terms of the balance between the hydrophobic and hydrophilic portions of the molecule. An empirical scale of hydrophile-lipophile balance numbers (HLB) has been devised. An HLB number is a value extending from 1 to approximately 50, which indicates the extent of hydrophilicity or lipophilicity of a surface-active agent. The more hydrophilic surfactants have high HLB numbers (in excess of 10), whereas surfactants with HLB numbers from 1 to 10 are considered to be lipophilic.

Preferable biocompatible non-ionic polymeric detergents in the formulations of this invention have hydrophile-lipophile balance (HLB) numbers in the range of from about 10 to about 40, preferably from about 15 to about 35, and more preferably from about 12 to about 30. Further, such biocompatible non-ionic polymeric detergents are preferably selected from the group comprising ethoxylated fatty alcohol ethers and lauryl ether, octylphenoxy polyethoxy ethanol compounds, modified oxyethylated and/or oxypropylated straight-chain alcohols, polyethylene glycol monooleate compounds, polyoxyethylene sorbitan fatty acid esters, phenolic fatty alcohol ethers and block copolymers of propylene oxide and ethylene oxide (polyoxypropylene and polyoxyethylene condensates).

Further, preferably the biocompatible non-ionic polymeric detergents employed as stabilizers/solubilizers in the formulations of the instant invention include:

1. a mixture of ethoxylated fatty alcohol ethers and lauryl ether having the formula:

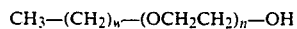

$$CH_3-(CH_2)_w-(OCH_2CH_2)_n-OH$$

wherein n is a distribution from about 1 to about 30, and Preferably centering on n=12, and w is a distribution from about 9 to about 17, containing a significant proportion of w=11; more preferably wherein said mixture of ethoxylated fatty alcohol ethers and lauryl ether is known as polyoxyethylene 12 lauryl ether or polyoxyethylene 12 lauryl alcohol; still more preferably said mixture is selected from the group of commercially available detergents known as Trycol ® LAL-12, Macol ® LA-12 and Siponic ® L-12, most preferably Macol ® LA-12;

2. an octylphenoxy polyethoxy ethanol compound having the formula:

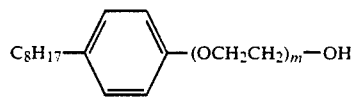

wherein m is an integer between about 5 and about 60, more preferably wherein m is an integer between about 20 and about 50, still more preferably wherein m is an integer between about 30 and about 40, further more preferably wherein m is either 30 or 40; most preferably wherein m is 30, the detergent is Triton ® X305, and wherein m is 40, the detergent is Triton ® X405;

3. a mixture of modified oxyethylated and/or oxypropylated straight-chain alcohols having the formulas:

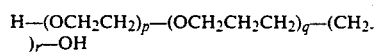

$$H-(OCH_2CH_2)_p-(OCH_2CH_2CH_2)_q-(CH_2)_r-OH$$

wherein p is an integer between about 1 and about 10; wherein q is zero or an integer between about 1 and about 10; and wherein r is an integer between about 6 and about 14; more preferably, wherein p is an integer between about 1 and about 5, q is zero or an integer between about 1 and about 5; and r is an integer between about 10 and about 12, most preferably when said detergent is Plurafac ® C-17;

4. a polyethylene glycol monooleate compound having the formula:

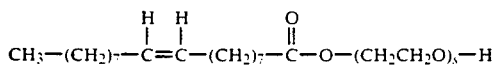

wherein s is an integer between about 1 and about 10, and wherein the molecular weight of said compound is in the range of from about 300 to about 750; more preferably, wherein s is an integer between about 2 and about 6, and wherein the molecular weight of said compound is from about 350 to about 550; still more preferably, wherein s is 3 and the molecular weight of said compound is about 400; and most preferably, wherein said detergent is Nopalcol ® 4-0;

5. a polyoxyethylene sorbitan fatty acid ester compound having the formula:

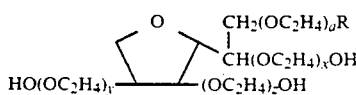

wherein the sum of the integers a, x, y and z equals 20 and R is a fatty acid having from about 10 to about 20 carbon atoms; more preferably wherein R is a fatty acid having from about 12 to about 18 carbon atoms; more preferably, laurate and oleate esters of sorbitol and sorbitol anhydrides copolymerized with about 20 moles of ethylene oxide for each mole of sorbitol and sorbitol anhydride; still more preferably, wherein R is lauric acid, said ester is a polysorbate 20 compound and is most preferably Tween ® 20, and wherein R is oleic acid, said ester is a polysorbate 80 compound and is most preferably Durfax ® 80 or Tween ® 80, most preferably Tween ® 80;

6. a phenolic fatty alcohol ether having the formula:

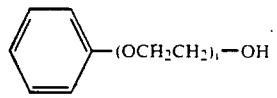

wherein v is an integer between about 10 and about 200, more preferably, wherein v is an integer between about 50 and about 150, and most preferably, wherein v is about 100 and said ether has an HLB of about 19; and 7. block copolymers of propylene oxide and ethylene oxide which are Pluronic polyols; more preferably, wherein said detergent is Pluronic ® F68.

Trycol ® LAL-12 has an HLB of about 14. Plurafac ® C-17 has an HLB of about 16. Nopalcol ® 4-0 has an HLB of about 12. Durfax ® 80 has an HLB of about 15.9. Tween ® 20 has an HLB of about 16.7. Tween ® 80 has an HLB of about 15. Triton ® X305 has an HLB of about 17.3. Triton ® X405 has an HLB of about 17.9. Pluronic ® F68 has an HLB of about 29. Macol ® LA-12 and Siponic ® L-12 both have HLBs of about 14.5.

Laureth 12 detergents are defined herein as non-ionic biocompatible polymeric detergents which are mixtures of ethoxylated fatty alcohol ethers and lauryl ether, having the formula outlined above under 1. Herein the terms Laureth 12, polyoxyethylene 12 lauryl ether and polyoxyethylene 12 lauryl alcohol, POE (12) lauryl ether and POE (12) lauryl alcohol are considered interchangeable. Preferred brand names of such Laureth 12 detergents are Macol ® LA-12, Trycol ® LAL-12 and Siponic ® L-12, wherein Macol ® LA-12 is most preferred.

The above-noted biocompatible non-ionic polymeric detergents are all commercially available from companies addressed in the USA as follows:

| | |
|---|---|
| Durfax ® 80 | Tween ® 80 |
| SCM Durkee Foods | ICI Americas Inc. |
| Huntington Bldg. | New Murphy Rd. & |
| 925 Euclid Avenue | Concord Pike |
| Cleveland, OH 44115 | Wilmington, DL 19897 |
| Plurafac ® C-17 | Pluronic ® F68 |
| BASF Wyandotte Corp. | BASF Wyandotte Corp. |
| 100 Cherry Hill Road | 101 Cherry Hill Road |
| Parsippany, N.J. 07054 | Parsippany, N.J. 07054 |
| Nopalcol ® 4-0 | Siponic ® L-12 |
| Diamond Shamrock | Alcolac Inc. |
| Process Chemicals Division | 3440 Fairfield Road |
| 350 Mt. Kemble Avenue | Baltimore, MD 21226 |
| Morristown, N.J. 07960-1931 | |
| Triton ® X305 and Triton ® X405 | Macol ® LA-12 |
| Rohm and Haas Delaware Valley Inc. | Mazer Chemicals, Inc. |
| 5000 Richmond Street | 3938 Porett Drive |
| Philadelphia, PA 19105 | Gurnee, IL 60031 |
| Trycol ® LAL-12 | |
| Emery Chemicals | |
| P.O. Box 628 | |
| Mauldin, S.C. 29662 | |

Further biocompatible non-ionic polymeric detergents having the above-noted parameters can be found in editions of McCutcheon's Emulsifiers & Detergents published by the McCutchion Division of MC Publishing Co; 175 Rock Road, Glen Rock, N.J. (USA). Such non-ionic polymeric detergents can be selected for the formulations of this invention by the screening processes herein outlined. Further, said screening processes can be used to test candidate non-ionic detergents singly or in combination with or without another solubilizing and/or stabilizing agent, preferably, SDS or glycerol.

Suppliers of several of the biocompatible non-ionic polymeric detergents included as solubilizers/stabilizers of this invention reported the results of toxicity studies performed by them as follows:

| | Reported Toxicology |
|---|---|
| Durfax ® 80 | No toxic effects when given at 1 g/day for 10 months in rhesus monkey. |
| Trycol ® LAL(12) | Acute oral $LD_{50}$ 2.2 g/kg in rabbit. |
| Nopalcol ® 4-0 | Acute oral $LD_{50}$ is greater than 21.5 ml/kg in rat. Intravenous $LD_{50}$ is 1.08 g/kg in mice. |

Example X, infra, confirms the essentially non-toxic nature of the biocompatible, non-ionic polymeric detergents employed as stabilizers/solubilizers in the formulations of this invention.

Specific examples of preferred combinations of non-ionic biocompatible polymeric detergents that are successful solubilizers/stabilizers of a normal dose (0.25 mg/ml) of recombinant IFN-$\beta$ include the combination of 0.15% polyoxyethylene 12 lauryl ether (preferably, selected from the group consisting of Trycol ® LAL-12, Siponic ® LA-12 and Macol ® LA-12) and 0.05% Nopalcol 4-0; 0.1% Triton X-305/0.05% Nopalcol 4-0; and 0.1% Triton X405/0.05% Nopalcol 4-0.

The formulations of this invention are in liquid form or lyophilized. Considered first herein are liquid formulations.

The liquid formulations are preferably maintained at a temperature range of from about −70° C. to about +10° C. The frozen formulations are preferably maintained at a temperature range of about −70° C. to about −20° C., whereas the stabilized liquid formulations are preferably maintained at a normal refrigeration range, preferably from about +2° C. to about +8° C.

The liquid formulations of this invention comprise:
1) recombinantly produced, purified IFN-$\beta$;
2) one or more biocompatible non-ionic polymeric detergents or a combination of one or more non-ionic detergents with another solubilizing and/or stabilizing agent; and
3) a small amount of buffer that maintains the formulation at a physiologically acceptable pH range.

The liquid formulations allow for the use of glycerol, an alternative solubilizing and/or stabilizing agent that is not a non-ionic detergent but when used in combination with one or more non-ionic detergents reduces the concentration of the non-ionic detergents required to solubilize/stabilize the IFN-$\beta$ by an order of magnitude. Without the presence of glycerol, the preferred concentration ranges for the biocompatible polymeric non-ionic detergents in the formulations of this invention as a solubilizer/stabilizer are from about 0.005% to about 5%, preferably from about 0.01% to about 3%, and more preferably from about 0.05% to about 1.5%. (The concentration ranges for the non-ionic detergent solubilizers/stabilizers of this invention are on a volume/volume basis except for the block copolymers of propylene oxide and ethylene oxide, such as the Pluronic polyols, for which the concentration ranges are on a weight/volume basis.) However, when glycerol is present in the liquid formulations of this invention at a concentration range by volume of from about 5% to about preferably from about 20% to 30% and more preferably about 25%, the one or more non-ionic detergents acting in combination with the glycerol need only be at one-tenth of the concentrations stated above, and the preferred concentration ranges for such non-ionic detergents, alone or in combination, are from about 0.0005% to about 5%, preferably 0.001% to about 1%, and more preferably from about 0.01% to about 0.5%.

The other preferred additional solubilizing and/or stabilizing agents that can be used in combination with one or more non-ionic detergents of this invention are stronger solubilizing and/or stabilizing agents, preferably sodium dodecyl sulfate (SDS), which can be used in both liquid and lyophilized formulations. Only very small amounts of such a stronger solubilizing and/or stabilizing agent is required in combination with one or more non-ionic detergents to prevent the IFN-$\beta$ from precipitating from the liquid or lyophilized/reconstituted formulations of this invention, and preferably SDS would be in a concentration range of from about 100 to 200 $\mu$g/mg of recombinant IFN-$\beta$, more preferably from about 150 to 200 $\mu$g/mg of recombinant IFN-$\beta$, and still more preferably from about 150 to about 173 $\mu$g/mg of recombinant IFN-$\beta$. Such a stronger solubilizing and/or stabilizing agent as SDS also acts to reduce the concentration of non-ionic detergents required to solubilize and stabilize IFN-$\beta$ at neutral pH.

Certain non-ionic detergents cannot stabilize/solubilize IFN-$\beta$ adequately to prevent precipitation of the IFN-$\beta$ without the addition of either glycerol or small amounts of SDS. Exemplary are the polysorbate compounds Durfax ® 80 and Tween ® 80, and the Pluronic polyol, Pluronic ® F68, which require such an additional solubilizer and/or stabilizer as SDS or glycerol, to maintain the IFN-$\beta$ in solution at the concentration ranges outlined herein. For example, Durfax ® 80 or Tween ® 80 at a concentration (volume/volume) of from about 0.05% to about 0.15%, preferably about 0.1%, successfully solubilizes and stabilizes normal dosage of recombinantly produced and purified IFN-$\beta$ in the presence of SDS at a concentration of from about 150 to about 200 $\mu$g/mg of IFN-62; and about 0.01% of such non-ionic detergents effectively solubilizers/stabilizers a normal dosage of IFN-$\beta$ in the presence of about 25% glycerol. The screening methods outlined below anticipate a protocol that encompasses testing candidate non-ionic detergents with such additional solubilizing and/or stabilizing agents as SDS and glycerol.

The liquid formulations can further comprise an additional stabilizing agent, preferably one or more carbohydrates, and more preferably one or more sugars. Preferred stabilizing agents include, for example, sucrose, dextrose, dextran, mannitol, sorbitol, inositol, fructose, galactitol, xylitol, lactose, and trehalose. More preferred are dextrose and mannitol, and most preferred is dextrose. Additional non-carbohydrate stabilizing agents can include, for example, human serum albumin (HSA), which can be used alone or in combination with a carbohydrate stabilizing agent, and glycine, which is preferably used in combination with a carbohydrate stabilizing agent. Such stabilizing agents are preferably in a concentration (weight/weight) range of from about 0.025% to about 10%, preferably from about 0.05% to about 7%, and more preferably from about 0.1% to about 5%.

The buffer selected to maintain the liquid formulations at a physiologically acceptable pH range is preferably at a concentration from about 1 to about 50 mM, more preferably from about 10 to about 25 mM.

The lyophilized formulations of this invention comprise: 1) recombinantly produced, purified IFN-$\beta$; 2) one or more non-ionic detergents or a combination of one or more non-ionic detergents and an additional lyophilizable solubilizing and/or stabilizing agent; 3) a carrier; and 4) a small amount of buffer that provides a physiologically acceptable pH range upon reconstitution.

The lyophilizable additional solubilizing/stabilizing agent is preferably SDS (at the concentrations indicated above for liquid formulations). Glycerol at the concentration ranges employed in the compositions of this invention is considered a non-lyophilizable additional solubilizing and/or stabilizing agent, and, therefore, the concentrations of non-ionic detergents in the lyophilized formulations of this invention are those essentially as outlined above for liquid formulations in the absence of glycerol.

The carrier in said lyophilized formulations can include the carbohydrate stabilizers either alone or in combination as outlined above for liquid formulations and in similar concentration ranges as well as human serum albumin alone or in combination with said carbohydrate stabilizers; however, such a selected carrier must not only have a stabilizing effect but also must provide bulk to the lyophilized product and is, therefore, herein termed a bulking/stabilizing agent. Preferred bulking/stabilizing agents, at preferred concentration ranges by volume noted in parentheses, include dextrose alone (about 1% to about 10%, more preferably, about 2% to about 5%); the combination of dextrose (about 0.1% to about 5%, more preferably about 0.1% to about 0.2%) with mannitol (about 0.5% to about 5%, more preferably about 1% to about 3%; or with human serum albumin (HSA) at a concentration from about 1% to about 5%, more preferably about 1% to about 2%; and HSA alone (preferably from about 1 to about 5%, more preferably about 2.5%). More preferred bulking/stabilizing agents are dextrose, preferably at a concentration of about 5%, and a combination of dextrose and mannitol at a concentration ratio by volume of from about 1/5 to about 1/20 (dextrose/mannitol), and more preferably at a concentration ratio of about 1/10. Such combinations of dextrose and mannitol are the most preferred bulking/stabilizing agents of the lyophilized formulations of this invention.

For lyophilized formulations, the buffer is preferably selected from buffers, such as citrate, maleate, acetate and phosphate, more preferably acetate or phosphate, and still more preferably phosphate, at the same preferred concentration range as indicated above for liquid formulations. Further, for lyophilized formulations, it is preferred that the pH of the composition to be lyophilized (preferably, the IFN-$\beta$ desalted pool) be maintained in the preferred range of 3.5 to about 6.5, more preferably from about 4 to about 6.0, and still more preferably about 6, to prevent the creation of aggregates during the formulation process because of any time delays necessitated by manufacturing requirements. However, if lyophilization is to be performed within about an hour, preferably less than an hour after neutralization (or if the formulation is liquid), the pH of the formulations can range from about 3.5 to about 9.5, preferably from about 4 to about 8, more preferably from about 5.5 to about 7.5, and still more preferably from about 6.0 to about 7.2.

Both the liquid and lyophilized formulations of this invention can further contain a minor amount of preservative to enhance chemical stability.

The particular biocompatible polymeric non-ionic detergents employed and the concentration thereof depend mainly on the particular IFN-$\beta$ protein or analog to be formulated, the presence or absence of an additional solubilizing and/or stabilizing agent (most notably glycerol), the concentration of the IFN-$\beta$, and pH of the formulation. The optimal concentration of the non-ionic detergent depends upon the pH of the formulation. For example, when Trycol ® LAL-12 or Plurafac ® C-17 are employed alone as a solubilizer/stabilizer of normal dosage compositions of IFN-$\beta$ at pH 5.0, both non-ionic detergents at concentrations as low as 0.01% can solubilize IFN-$\beta$. At pH 7.0, 0.15% Trycol ® LAL-12 can solubilize normal dosage IFN-$\beta$ compositions with only minor aggregation. Plurafac ® C-17 at 0.05% concentration can solubilize normal dosage IFN-$\beta$ compositions at pH 6. In general, the lower the pH of the formulation, the lower the concentration of the non-ionic detergent that is necessary to solubilize/stabilize it.

Further, the concentration of the biocompatible, non-ionic, polymeric detergent varies with the concentration of IFN-$\beta$ in the formulation. For example, a high dosage formulation of IFN-$\beta$ is that which contains about 1 to about 2 mg/ml of IFN-$\beta$ in the final container vial (2 to $4 \times 10^8$ units per mg). A normal dosage formulation has 0.25 mg/ml of IFN-$\beta$ in the final container vial ($0.5 \times 10^8$ units per mg), whereas, a low dosage formulation has 0.125 mg/ml of IFN-$\beta$ in the final vial ($0.25 \times 10^8$ units per mg). The preferred concentration range of the solubilizer/stabilizer containing one or more non-ionic detergents for a high dosage formulation is from about 0.1% to about 5%, preferably 0.25% to about 3%, and more preferably from about 0.5% to about 2.0%. For the normal dosage formulations of IFN-$\beta$, the preferred concentration range of the non-ionic detergent is from about 0.005% to about 1.0%, more preferably 0.075% to about 0.5%, and still more preferably from about 0.01% to about 0.3%.

Lower dosage formulations of IFN-$\beta$ would similarly require lower concentration ranges of the biocompatible non-ionic polymeric detergent employed.

A most preferred example of a lyophilized normal dose formulation of this invention comprises:

0.25 mg/ml recombinant IFN-$\beta$
0.15% (volume/volume) polyoxyethylene 12 lauryl ether;
20 mM sodium phosphate buffer;
0.2% dextrose; and
2% mannitol.

It is preferred that the polyoxyethylene 12 lauryl ether is Macol ® LA-12.

Many of the methods used for the recovery of lipophilic recombinant proteins, such as bacterially produced IFN-$\beta$, utilize SDS or similar surfactants as the primary solubilizing agents for the solubilization and isolation of the protein from the cellular material and subsequent acid precipitation to obtain the protein. By further purification techniques carried out at or near neutral pH, the SDS levels in the final protein preparations are reduced to about 0.1%. Further removal by diafiltration or desalting techniques in the 3–8 pH range does not follow first-order kinetics due to protein SDS interactions which significantly affect the kinetics of SDS removal. It was found that SDS removal from recombinant proteins promotes protein-protein interactions at the pH range of 3–8 that result in aggregation or precipitation of the protein and consequent loss of activity.

One solution to the problem of such aggregation and precipitation during SDS removal is described in U.S. Pat. No. 4,462,940 discussed above, and said patent is herein incorporated by reference. That procedure uses a high pH range (10.5 to 12.5) during diafiltration and desalting. Although the procedure o the '940 patent, as well as any other procedures known in the art, can be used to provide purified IFN-$\beta$ for formulation with the stabilizers/solubilizers of this invention, as well as any other recovery, isolation and purification procedures known in the art, the procedures outlined herein are considered the most preferred procedures known to the applicants.

The instant invention solves the problem of IFN-$\beta$ aggregation, precipitation and loss of protein activity with the removal of SDS or similar solubilizing agents by methods that further avoid the high alkaline pH range (10.5 to 12.5) of the '940 patent.

Therefore, one aspect of the invention is to avoid such high pH diafiltration or desalting conditions by employing a milder detergent or chaotrope as a transfer component during diafiltration or desalting, preferably desalting, to replace stronger solubilizing agents such as SDS used in the extraction and purification of the recombinant IFN-$\beta$ from the host microorganisms. Such milder detergent/chaotropes used as transfer components allow for diafiltration or desalting of the IFN-$\beta$ to occur at a lower pH range, for example, from about pH 8.5 to about 10, preferably from about 9- 9.5. Examples of such detergent/chaotropes for use as transfer components include fatty acid salts having carbon chains of from about 10 to 13 carbons, preferably 11 to 12 carbons, and most preferably 12 carbons. It is preferred that the fatty acid salt be a laurate salt and most preferred that such laurate salt be sodium laurate.

The concentration range of said transfer component in an elution buffer, preferably a low ionic strength elution buffer, is from about 0.05% to about 2%, preferably 0.1% to 1% (volume/volume).

In addition to such fatty acid salts, a number of other mild detergent/chaotropes can be used such as, for example, urea (5-7 molar, preferably 6M) or, more preferably, guanidine hydrochloride (5-7 molar, preferably 6M).

Further, it is possible to use the non-ionic biocompatible polymeric detergents of this invention as transfer components as well as a solubilizer/stabilizer, providing that the pH and other protocol conditions are optimized for each of the individual non-ionic detergent-containing solubilizers/stabilizers employed.

The pH of the thus purified IFN-$\beta$ pool, that is after diafiltration or desalting, preferably desalting, wherein a low ionic strength elution buffer containing a transfer component is employed, is then adjusted to a level of about 2 to 4, preferably 3 to 4, and most preferably about 3.0, at which point the transfer component, preferably sodium laurate, will precipitate from the solution. The precipitated transfer component is then removed by filtration and/or centrifugation or by other means known to those skilled in the art.

The representative process described in Example 1 infra was found to remove the sodium laurate transfer component to levels below the detection limit (that is, approximately 10 moles of laurate per mole of IFN-$\beta$) of an assay employing a standard protein RP-HPLC system with low wavelength UV detection.

The stabilizer/solubilizer containing one or more biocompatible non-ionic polymeric detergents, and optionally another solubilizing and/or stabilizing agent, can then be added to the protein pool. Optionally, said mixture can be held before raising the pH to between 3.5 and 9.5, preferably 4.0 and 8.0, and more preferably 5.5 and 7.5. The amount of time that the solution may be held depends mainly on the particular IFN-$\beta$ analog, the particular composition of the stabilizer/solubilizer employed, the exact pH, and the concentrations of IFN-$\beta$ protein and stabilizer/solubilizer composition, and typically ranges from 0-240 minutes, preferably 10-180 minutes.

A further aspect of this invention is to provide for extraction, purification and formulation processes wherein the formulated recombinant IFN-$\beta$ is totally or substantially free of SDS or other less desired solubilizing agents. Said improved processes comprise the use of a non-toxic, milder detergent/chaotrope as the primary solubilizing agent instead of SDS or other strong chemical solubilizing agents during extraction, purification and recovery of the recombinant IFN-$\beta$. Such non-toxic detergent/chaotropes include the fatty acid salts discussed above as transfer components, preferably laurate salts, and most preferably sodium laurate (0.5% to 3%, preferably 1-2%). The preferred pH range for such fatty acid salt solubilizers would be between 9 and 10, inclusively, more preferably between 9 and 9.5, inclusively.

It is preferred that when a fatty acid salt, such as sodium laurate, is employed as the primary solubilizing agent, it be in a buffer, such as phosphate, Tris HCl, or an acetate buffer wherein said buffer is in a molarity range of from about 5 to 40 mM, preferably 10-30 mM, and most preferably about 20 mM. It is further preferred that the solubilization process be performed slowly over an extended period of time from about 1 to 24 hours, and that sonication be performed to promote solubilization. Preferably, reducing agents, such as dithiothreitol (DTT) or $\beta$-mercaptoethanol ($\beta$-mer), can also be employed with the fatty acid salt to promote solubilization.

Other milder detergent/chaotropes useful as primary solubilizing agent alternatives include guanidine hydrochloride (4-8M, preferably 5-7M, most preferably about 6M) with a reducing agent such as DTT or $\beta$-mercaptoethanol ($\beta$-mer) (30-70 mM, preferably 40-60 mM, most preferably about 50 mM).

When such a fatty acid salt or guanidine hydrochloride is employed as the primary solubilizing agent as an alternative to a detergent, such as SDS, it is preferred that the refractile bodies containing the recombinant interferon-$\beta$ be at a concentration of about 15 to 5 mg/ml, more preferably about 10 to 5 mg/ml, and still more preferably about 8 mg/ml. When such primary solubilizing agents are used, the formulations produced are totally or substantially free of SDS.

The use of a fatty acid salt, such as sodium laurate, provides a further method of avoiding highly alkaline conditions and the problems of aggregation, precipitation and loss of activity of the IFN-$\beta$ during diafiltration or desalting. When such a fatty acid salt as sodium laurate is used as the primary solubilizing agent during recovery and purification, it is unnecessary to desalt or diafilter the IFN-$\beta$ pool as the last step of purification unless there is a need to remove other low molecular weight components such as EDTA. Once the IFN-$\beta$ has been purified sufficiently, the pH of the IFN-$\beta$ pool can be lowered to about 2 to 4, preferably 3 to 4, and more preferably 3 to 3.5, at which point the fatty acid salt precipitates. The precipitate can be removed by centrifigation and filtration or by other means known to those skilled in the art. Then the IFN-$\beta$ solution can be stabilized with an appropriate solubilizer/stabilizer of this invention, and the pH thereof can be adjusted to that desired for the formulation. If said pH adjustment is to a level above 6.5, preferably in immediate continuous sequence a bulking/stabilizing agent is added, and the solution, optionally pre-filtered and sterile filtered, is lyophilized. As indicated above, "immediate" is defined herein to mean less than an hour. If the pH is 6.5 or below, preferably 6 or below, the sequence of adding the bulking/stabilizing agent and lyophilizing the optionally pre-filtered and sterile filtered solution need not be immediate.

It is preferred, when dextrose is used as the carrier for lyophilized formulations of this invention, that the lyophilization cycle be performed as a slow, two-stage ramp. A preferred lyophilization protocol used when dextrose is the carrier is exemplary and follows:

(a) freeze for 4 hours at $-30°$ C.;
(b) lyophilize at that temperature for 24 hours;
(c) ramp at $6°$ C./hour to $+5°$ C.;
(d) hold at $+5°$ C. for 12 hours;
(e) ramp to $+15°$ C. at $6°$ C./hour; and
(f) hold at $+15°$ C. for at least 12 hours.

The freezing time of step (a) can be from about 2 to about 6 hours at a temperature range from about −70° C. to about −20° C. The lyophilizing time of step (b) can be from about 12 to about 48 hours. The ramping rate for steps (c) and (e) can be from about ° C/hour to about 12° C./hour to respective temperature ranges of from about −5° C. to about +10° C. (steps c and d) and from about +10° C. to about +25° C. (step e). The holding time period for step (d) can be from about 6 to about 18 hours.

Further, this invention provides for methods of screening known biocompatible non-ionic polymeric detergents, combinations of said detergents, and combinations of one or more of said detergents with another solubilizing and/or stabilizing agent to find stabilizers/solubilizers for the recombinant IFN-β formulations of this invention. A preferred example of such a screening method comprises the steps of:

(a) passing extracted, purified recombinant IFN-β in 0.1% SDS on a desalting column equilibrated in 0.1% sodium laurate in an elution buffer at pH 9.0–10.0;

(b) lowering the pH of the eluate with an appropriate acidic agent to about pH 2–4;

(c) adding an appropriate concentration of the candidate biocompatible non-ionic polymeric detergent, of a candidate combination of said detergents, or of a candidate detergent or combination of said detergents with another solubilizing and/or stabilizing agent to the desalted pool;

(d) adjusting the pH to 3.5 to 9.5 with an appropriate basic agent; and (e) allowing said solution to stand for 24 hours at pH 3.5 to 9.5.

The term purified recombinant IFN-β in the screening step (a) above preferably refers to IFN-β that has been purified according to the procedures described in Example 1 below and outlined in Schemes 2A and 2B through the sizing step of the G-75 column. However, such a screening method is exemplary and other screening methods employing other methods of purifying recombinantly produced IFN-β are within the scope of this invention.

If the candidate stabilizer/solubilizer maintains the recombinant IFN-β in solution at pH 3.5 to 9.5 over a 24-hour period, it is considered for inclusion in the prototype formulations of this invention.

A preferred screening process includes the step of filtering from the desalted IFN-β pool the precipitated sodium laurate which precipitates in step (b).

A further preferred screening method of this invention is that wherein the pH range for step (a) is 9–9.5, for step (b) is 3–4 and other steps (d) and (e) are performed at the pH range of about 4 to about 8. A still further preferred screening method is that wherein the pH range for step (a) is 9–9.2, for step (b) is about 3 to about 3.5, and wherein steps (d) and (e) are performed at the pH range of about 5.5 to about 7.5.

The elution buffer of step (a) is preferably Tris-HCl at pH 9 to 9.8; borate at pH 9.0 to 9.8; sodium phosphate at pH 9.0 to 9.8; acetate at PH 9.0 to 9.8; or sodium pyrophosphate at pH 9.0 to 9.8.

The following Screening Flow Chart graphically illustrates further exemplary methods of screening formulation reagents for the IFN-β pharmaceutical compositions of this invention. The terms G-75 and G-25 are gel filtration columns, which are positioned in a representative IFN-β purification process according to Example 1, infra.

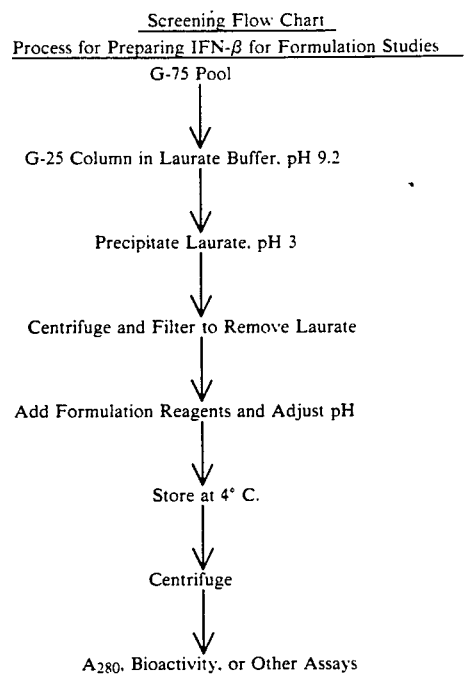

Screening Flow Chart
Process for Preparing IFN-β for Formulation Studies

G-75 Pool
↓
G-25 Column in Laurate Buffer, pH 9.2
↓
Precipitate Laurate, pH 3
↓
Centrifuge and Filter to Remove Laurate
↓
Add Formulation Reagents and Adjust pH
↓
Store at 4° C.
↓
Centrifuge
↓
$A_{280}$, Bioactivity, or Other Assays To analyze prototype formulations, ultracentrifugation is used as a simple method of detecting the presence of high molecular weight aggregates. Such candidate formulations can also be screened by SDS-PAGE under non-reducing conditions and Western blots.

The preferred range of recombinant IFN-β in such formulations is from about 0.05 mg/ml to about 10 mg/ml, more preferably 0.1 mg/ml to about 5 mg/ml, and still more preferably 0.1 mg/ml to about 2.0 mg/ml.

A preferred process for preparing lyophilized IFN-β formulations of this invention comprises the steps of: (a) extracting the recombinant beta-interferon from the disruptate of a host organism ? -Z transformed to produce the protein; (b) purifying the IFN-β protein using as the last purification step a desalting step at a pH range of about 8.5 to 10 employing 0.05 to 2% sodium laurate as a transfer component; (c) lowering the pH of the desalted pool with an appropriate acidic agent to a pH of about 2 to about 4; (d) removing the precipitated sodium laurate by centrifugation and filtration; (e) adding to the desalted pool an effective amount of one or more non-ionic biocompatible polymeric detergents, or a combination of one or more biocompatible non-ionic polymeric detergents with another solubilizing and/or stabilizing agent to stabilize/solubilize the IFN-β; (f) adjusting the pH of the pool with an appropriate basic agent to a range of between 3.5 and 9.5; (g) adding an effective amount of a bulking/stabilizing agent; (h) prefiltering and sterile filtering the solution; and (i) lyophilizing the formulation.

Preferably, if the pH adjustment in step (f) is to a level above 6.5, steps (f) through (i) are carried out in rapid, continuous succession to avoid the creation of IFN-β aggregates. It was found that freezing the sample immediately after neutralization to pH 6.5 and above in dry ice and ethanol did not produce aggregates, whereas freezing the samples slowly by placing the room temperature samples at −20° C. caused some degree of aggregation. When formulations were neutralized to a pH at or above 6.5 four hours before lyophilization, a 30% to 40% increase in the amount of aggregation was obtained when compared to samples that were neutralized immediately (within an hour) before lyophilization. Therefore, it is preferred that lyophilization be performed immediately after neutralization to pH 6.5 and above, which results in very low levels of aggregates. However, when the neutralization in step (f) is to pH 6.5 or below, more preferably at or below pH 6.0, there is no significant aggregation in samples left at room temperature for 24 hours before lyophilization.

Further, preferably, the desalting step is carried out at a pH range of from about 9 to 9.5. Also preferably, the pH range of step (c) is 3 to 4, and more preferably about pH 3.0 and for step (f) is 4-8, more preferably 4.0 to 6.5, and still more preferably 4.0 to 6.0. Further, preferably, the pH range for step (c) is about 3.5, and for step (f) is from about 5.5 to about 6.5.

In preferred embodiments of the invention, the nonionic biocompatible polymeric detergent stabilizers/solubilizers or combinations thereof are Laureth 12 detergents, Plurafac® C-17, Laureth 12/Nopalcol in about a 2:1 volume ratio, or Triton X305 or X405/Nopalcol in a 2:1 volume ratio. Further, a preferred embodiment wherein another solubilizing agent other than a non-ionic biocompatible polymeric detergent is employed is Durfax® 80 or Tween® 80 at about 0.1% with SDS wherein the SDS is in a concentration range of from about 150 μg to about 200 μg per mg of IFN-β, preferably 150 μg to about 173 μg per mg of IFN-β. Further, preferred is the concentration of about 0.01% of any of the preferred non-ionic detergents (including Pluronic® F68) with glycerol at a concentration of about 25%.

For purposes of practicing the present invention, bacteria are the preferred microorganism hosts, with *E. coli* being the most preferred.

In general, the recovery, purification and formulation processes herein involve fermenting the host organism transformed to express the IFN-β, disrupting the cell wall and cell membrane of the host organism, separating the refractile material containing the recombinant IFN-β from the rest of the cellular debris, solubilizing the refractile material in an aqueous buffer under reducing conditions, extracting the IFN-β with 2-butanol or 2-methyl-2-butanol, subjecting the extracted IFN-β to chromatographic purification, and then diafiltering or desalting, preferably desalting, the IFN-β to remove the solubilizing agent optionally using a suitable transfer component and formulating as described above.

Schemes 1A and 1B outline the steps of a preferred embodiment of the invention for extracting, purifying and formulating microbially produced IFN-β. In this flow chart, sodium laurate is used as the primary solubilizing agent in the extraction and purificaiton process and as a transfer component.

SCHEME 1A

| | |
|---|---|
| Fermentation | |
| Cell concentration | |
| Cell wall and membrane disruption | homogenization |
| Diafiltration | 5 mM EDTA |
| Redisruption | 2 mM EDTA; 1% octanol (v/v); homogenization |
| Sucrose suspension | 15-23% sucrose (w/w) |
| Centrifugation | 10.000-15,000 xg |
| Paste solubilization | 1-2% sodium laurate. 20 mM phosphate buffer. 50 mM DTT. pH 9-10 (with sonication) |

SCHEME 1A -continued

| | |
|---|---|
| Reduction | 10 mM DTT: 1-2% sodium laurate: 2 mM EDTA: pH 9; heat to 50° C. for 10 min. under nitrogen; cool to about 25° C. |
| Sephacryl® S200 column | 10 mM Tris.HCl; pH 9.2: 1-2% sodium laurate; 1 mM EDTA |
| Oxidation | Iodosobenzoic acid (IBA) equimolar: protein:IBA; 1-2% sodium laurate: 2 mM sodium pyrophosphate; pH 9; 1 mM EDTA |
| Concentration | pH 9.0 |
| Sephacryl® S200 column | 10 mM Tris.HCl; pH 9.2: 0.1-0.5% sodium laurate: 1 mM EDTA |

SCHEME 1B

| | |
|---|---|
| Concentration | 10 mM Tris.HCl; pH 9.2; 0.1-0.5% sodium laurate, 1 mM EDTA |
| Sephadex® G-75 column | 10 mM Tris.HCl; pH 9.2; .1-.5% sodium laurate; 1 mM EDTA |
| Sephadex® G-25 column | 0.1% laurate; 10 mM Tris.HCl; pH 9.2 |
| pH Adjustment | pH of eluate lowered quickly to 3 with 1.0 N HCl; sodium laurate precipitates |
| Centrifugation and Filtration | To remove precipitated sodium laurate |
| Stabilization | 0.15% Trycol LAL-12 added |
| Neutralization | pH raised to between 6.0 and 7.2 |
| Polyol addition | 5% dextrose |
| Pre-filtration | 0.45 μM |
| Sterile filtration | 0.22 μM |
| Lyophilization (immediate) | |
| Final Container Product | |

MACOL® LA-12 (0.15%) is the formulating agent (solubilizer/stabilizer in the formulation) and dextrose (5% is the bulking/stabilizing agent.

Schemes 2A and 2B outline another preferred embodiment of this invention wherein sodium dodecyl sulfate (SDS) is used as the primary solubilizing agent, and sodium laurate is used as a transfer component during a desalting step on a Sephadex® G-25 desalting column. PLURAFAC® C-17 (0.1%) is the formulating agent (solubilizer/stabilizer in the formulation) and dextrose (5%) is the bulking/stabilizing agent. Further, Schemes 2A and 2B illustrate the details of the individual process steps of the preferred embodiment of the present invention including the culture of the transformed microorganisms in an appropriate fermentation medium through the final step where the purified IFN-β is stabilized and then lyophilized and reconstituted into therapeutic formulations.

SCHEME 2A

| | |
|---|---|
| Fermentation | |
| Cell concentration | |
| Cell membrane disruption | homogenization |
| Diafiltration | 5 mM EDTA |
| Redisruption | 2 mM EDTA; 1% octanol (v/v); homogenization |
| Sucrose suspension | 15-23% sucrose (w/w) |
| Centrifugation | 10,000-15,000 xg |
| Paste solubilization | 2% SDS phosphate buffered saline |
| Reduction | 10 mM DTT: 2% SDS; 2 mM EDTA; pH 9; heat to 50° C. for 10 min. under nitrogen; cool to about 25° C.; adjust pH to 7.4 with glacial acetic acid |
| Organic extraction | 2-butanol/suspension (v/v) |
| Acid precipitation | pH 6.2: 2 mM DTT; 0.1% SDS |

SCHEME 2A

| | |
|---|---|
| Centrifugation | 10,000–15,000 xg |
| Acid precipitate solubilization | 2% SDS; 5 mM EDTA; 50 mM phosphate buffer |
| Reduction | 20 mM DTT; pH 8.5; heat to 50° for 10 min. under nitrogen; cool to about 25° C. |
| Sephacryl ® S200 column | 50 mM acetate; pH 5.5; 1% SDS; 1 mM EDTA |
| Oxidation | Iodosobenzoic acid (IBA) equimolar; protein:IBA; 0.1% SDS; 2 mM sodium pyrophosphate; pH 9; 1 mM EDTA |
| Concentration | pH 5.5 |
| Sephacryl ® S200 column | 50 mM acetate; pH 5.5; 0.1% SDS; 1 mM EDTA |

SCHEME 2B

| | |
|---|---|
| Concentration | |
| Sephadex ® G-75 column | 50 mM acetate; pH 5.5; 0.1% SDS; 1 mM EDTA |
| Sephadex ® G-25 column | 0.1% sodium laurate (transfer component) in 10 mM Tris-HCl, pH 9.2 |
| pH Adjustment | pH of eluate lowered quickly with 1.0 N HCl to pH 3; sodium laurate precipitates |
| Centrifugation and Filtration | To remove the precipitated sodium laurate |
| Stabilization | 0.1% Plurafac C-17 added |
| Neutralization | pH raised to between 6.0 and 7.2 |
| Polyol addition | 5% dextrose |
| Pre-filtration | 0.45 μM |
| Sterile filtration | 0.22 μM |
| Lyophilization (immediate) | |
| Final Container Product | |

The individual process steps of such an example of one embodiment of the instant invention are summarized as follows:

(a) growing the transformed bacterial hosts in an appropriate fermentation medium;

(b) concentrating the bacteria in the fermentation medium by cross-flow filtration, centrifugation or other conventional methods;

(c) disrupting the cell wall and cell membrane of the bacteria;

(d) removing greater than 99% by weight of the salts from said disruptate by diafiltration or centrifugation;

(e) redisrupting the desalted disruptate;

(f) adding a material to the disruptate to increase the density or viscosity of, or to create a density or viscosity gradient in, the liquid within the disruptate;

(g) separating the refractile material from the cellular debris by high-speed centrifugation;

(h) solubilizing the refractile material in an aqueous buffer containing a reducing agent;

(i) organically extracting the solubilized refractile material, preferably with 2-butanol or 2-methyl-2-butanol;

(j) isolating said refractile material from the extractant, preferably by employing an acid precipitation step followed by centrifugation;

(k) solubilizing the resulting IFN-$\beta$ particle pellet with distilled water or with an aqueous solution of SDS at a IFN-$\beta$ to SDS ratio of about 1:3;

(l) adjusting the pH of the solution to about 9.5 and reducing the solubilized IFN-$\beta$;

(m) purifying the reduced IFN-$\beta$ by chromatography;

(n) oxidizing the IFN-$\beta$ from step (m);

(o) further purifying the oxidized IFN-$\beta$ by gel chromatography and collecting the eluate containing the purified IFN-$\beta$;

(p) desalting the purified IFN-$\beta$ eluate in a desalting column equilibrated and run in 0.1% sodium laurate in 10 mM Tris-HCl at pH 9.2;

(q) lowering the pH of the eluate quickly to pH 3.0 with an appropriate acidic agent;

(r) centrifuging and filtering the IFN-$\beta$ pool;

(s) adding an effective amount of a non-ionic biocompatible polymeric detergent-containing solubilizer/-stabilizer;

(t) adjusting the pH of the solution to near physiological pH;

(u) adding an appropriate bulking/stabilizing agent in a concentration of from about 0.25% to about 10%;

(v) filtering the solution;

(w) immediately lyophilizing the IFN-$\beta$ sample; and (x) reconstituting the lyophilized IFN-$\beta$ sample, if desired.

Ten mM dithiothreitol may be optionally included in the initial solubilization step, and the mixture may be heated to about 50° C. for about 10 minutes. In addition, the IFN-$\beta$ is preferably oxidized so that its cysteine residues are bridged to form cystines, as described by U.S. Pat. No. 4,530,787 to Shaked et al; using o-iodosobenzoic acid solution or by U.S. Pat. No. 4,572,798 to Koths et al; entitled "Method for Promoting Disulfide Bond Formation in Recombinant Proteins," using copper chloride. Preferably, o-iodosobenzoic acid is employed for the oxidation.

In another preferred embodiment of the process of the invention, the disrupted cells are treated to isolate and purify the interferon-$\beta$ protein, and then the following steps are carried out: (a) desalting the IFN-$\beta$ protein by G25 chromatography at pH 9–9.2 employing an elution buffer containing 0.05 to 2% sodium laurate as a transfer component; (b) adjusting the pH of the desalted pool to about 3.5; (c) centrifuging and filtering to remove the precipitated transfer component; (d) adding the stabilizer/solubilizer composition to the desalted pool; (e) adjusting the pH of the IFN-$\beta$ mixture to neutral pH; (f) adding an effective amount of a bulking/stabilizing agent; (g) filtering the pool; (h) immediately lyophilizing the IFN-$\beta$ protein sample upon neutralization and bulking/stabilizing addition; and (i) reconstituting the lyophilized IFN-$\beta$ protein sample, if desired.

Herein incorporated by reference is the disclosure of EP 206,828 which details the procedure for extracting and purifying recombinant protein, such as IFN-$\beta$, which are deposited within the microbial host in refractile bodies. Said disclosure focuses on the isolation of the refractile materials by front-end processes which are termed either "abbreviated" or "expanded." A synopsis of said procedures follows.

The transformed microorganisms are grown in a suitable growth medium, typically to an optical density (OD) of at least about 30 at 680 nm, and preferably between about 20 and 40 at 680 nm. The composition of the growth medium will depend upon the particular microorganism involved. The medium is an aqueous medium containing compounds that fulfill the nutritional requirements of the microorganism. Growth media will typically contain assimilable sources of carbon and nitrogen, energy sources, magnesium, potassium and sodium ions, and optionally amino acids and purine and pyrimidine bases. (See *Review of Medical Biology*, Lange Medical Publications, 14th Ed pp. 80–85 (1980).) In expression vectors involving the trp promoter, the tryptophan concentration in the medium is carefully controlled to become limiting at the time IFN-$\beta$ expression is desired. Growth media for *E. coli* are well known in the art.

After the cells are harvested from the culture, they may be concentrated, if necessary, to about 20 to 150 mg/ml, preferably 80 to 100 mg/ml (OD 40 to 300, preferably 160 to 200 at 680 nm) by cross-flow filtration, centrifugation, or other conventional methods. Preferably a compound which is non-toxic to humans, such as 1-octanol, in an amount of about 1% by weight of total components, is added to the fermenter before or during cell concentration to ensure that no viable recombinant organism$ remain before containment is broken.

Following concentration of the harvested culture, the cell membranes of the microorganisms are disrupted. Conventional cell disruption techniques such as homogenization, sonication, or pressure cycling may be used in this step of the process. Preferred methods are sonication or homogenization with a homogenizer. The end point of the disruption step can be determined by monitoring the optical density with the absorbance at 260 nm of the suspension typically increasing with cell lysis. In any event, the disruption should break substantially all of the cells so that substantially no intact cells are carried through to the solubilization step. Before the disruption, the pH of the liquid phase of the concentrate is adjusted, if necessary, to a level that facilitates removal of *E. coli* proteins in subsequent steps, while retaining the heterologous protein as an insoluble complex in the cellular debris.

After the cells have been disrupted, deionized water is preferably added to the disruptate and greater than 99% by weight of the salts are removed therefrom. The removal of these salts to reduce the ionic strength of the disruptate may be accomplished by diafiltration using deionized water to flush out the ions or by centrifuging to pellet the cellular debris and refractile bodies followed by resuspension in deionized water.

After the salts are essentially removed, optionally a compound such as 1-octanol may be added to the desalted disruptate, if not added earlier, to ensure that no viable recombinant organisms remain. The desalted disruptate is again disrupted as described above for the initial disruption.

After redisruption, density or viscosity is increased and/or a gradient is created during centrifugation in the liquid within the disruptate by adding a material to the disruptate.

In the final step of the abbreviated "front-end" process to recover the refractile bodies, the refractile bodies containing the desired protein are separated from the cellular debris by high-speed centrifugation. By "high-speed centrifugation" is meant spinning the suspension in a centrifuge at about 10,000 to 40,000 times gravity, preferably about 10,000–20,000 × g, for a suitable time period depending on the volume, generally about 10 minutes to seventy-two hours. The pellet resulting from the centrifugation is called the "particle pellet" or "particle paste." The abbreviated front-end process is most preferably used when sodium laurate is the primary solubilizing agent.

In an alternative, expanded "front-end" process to recover the refractile bodies, the particle pellet obtained from the last centrifugation step of the abbreviated front-end process, is solubilized, reduced and then extracted from the aqueous medium with 2-butanol or 2-methyl-2-butanol. The extractant phase is then precipitated with an acid and centrifuged to produce a "final pellet" or "final paste", which is then further purified as indicated.

The alternative, expanded front-end process is distinguished from the abbreviated front-end process in that it comprises several additional steps as follows: solubilizing the refractile bodies under reducing conditions; organically extracting the solubilized refractile material; and isolating said refractile material from the extractant. Essentially, the enhanced purity of the final pellet as opposed to the particle pellet lessens the purifying burden of downstream processing. There is an interdependence between the choice of the front-end process and later process purification steps to achieve the desired purity level for the final product. Once the choice of the particular front-end recovery of the refractile bodies has been made, one skilled in the art can pick and choose the alternative purifying steps outlined below to achieve the desired purity level of the final product.

Whether the abbreviated or expanded front-end process is utilized to recover the refractile bodies containing the IFN-$\beta$, the next step in purification is solubilizing either the particle or final pellet containing the refractile material. The following solubilizing agents can be used: sodium dodecyl sulfate (SDS), sodium laurate, urea, sodium dodecyl sulfonate, sodium decyl sulfate, sodium tetradecyl sulfate, sodium tridecyl sulfonate, sodium dodecyl N-sarcosinate, sodium tetradecyl N-sarcosinate, sodium dioctylsulfosuccinate, and guanidine hydrochloride. Preferred solubilizing agents are SDS, sodium laurate or guanidine hydrochloride. Most preferred is sodium laurate or guanidine hydrochloride at concentrations and under the conditions indicated above to eliminate the possibility of SDS in the final container product.

The solubilizing agent is in an aqueous buffer, preferably phosphate buffered saline. The preferred percentage of the solubilizing agent is in the range of 1% to 5% (w/v). (Percentages herein reflect weight to volume ratios.) The preferred solubilizing solutions are phosphate buffered saline with 1–2% sodium laurate (20 mM NaPO$_4$) at pH 9–10 and 6 M guanidine hydrochloride in 50 mM $\beta$-mercaptoethanol. Sonication is preferably employed when either sodium laurate or guanidine HCl is employed as the solubilizing agent to promote solubilization.

Reducing agents that can be employed during the solubilization step include: $\beta$-mercaptoethanol ($\beta$-mer), glutathione, cysteine and dithiothreitol (DTT). DTT and $\beta$-mer are the most preferred reducing agents. It is preferred that reducing agents be employed when either sodium laurate or guanidine hydrochloride is used as the primary solubilizing agent.

The solubilization will typically be carried out at temperatures in the range of 20° C. to 25° C. with mixing to facilitate contact between the solid phase and the solubilizing medium. Optionally, a reduction step may be carried out at this point. The pH, if necessary, may be adjusted to a range of 8.5 to 10, most preferably approximately 9. The suspension may be heated to 50±5° C.

for 5 to 15 minutes under nitrogen. The reaction mixture would then be cooled to approximately 25° C.

The solubilization is considered complete when the sample has sat 15 minutes or the solution turns translucent. Optionally at this point, the insoluble material may be separated by centrifugation or filtration after completing the solubilization.

After the protein is solubilized, the resulting suspension may optionally be centrifuged at 10,000–40,000×g, preferably 10,000 to 15,000×g, to obtain a pellet containing, inter alia, additional host (e.g; $E.\ coli$) proteins, notably including certain contaminants that have molecular weights very close to that of the desired protein. The exact speed of centrifugation is not critical, as most of the insoluble material will come out, even at low speeds. The pellet is discarded and the supernatant containing the desired protein is retained and processed to recover the desired protein.

If a reduction step was not carried out during the solubilization, the next step in the process would be a reduction of the solubilized refractile body protein. A preferred reducing agent is dithiothreitol (DTT). Reduction conditions may also include the addition of a chelating agent such as ethylenediaminetetraacetic acid (EDTA).

The next step in the process is to separate the protein in the supernatant from any host contaminants remaining after the centrifugation or filtration and optimally from the solubilizing agent. Gel filtration chromatography, reverse-phase high performance liquid chromatography (RP-HPLC), or a combination of gel filtration chromatography and RP-HPLC, can be used. The gel filtration chromatography is preferably carried out in two stages that remove both pyrogenic components and protein contaminants having molecular weights higher or lower than that of the protein. Gels that are capable of fractionating the solution to permit separation of the protein from these contaminants are commercially available. Sephacryl ® S-200 is a preferred gel for removing the higher molecular weight components and Sephadex ® G-75 or G-100 gels are preferred for removing the low molecular weight contaminants. The gel filtrations will typically be run in buffered solutions (pH 5.5 to 7.0) containing about 0.1% to 1.5% solubilizing agent and about 0.5 to 10 mM reducing agent. The column will be sized to permit suitable resolution of the desired components.

RP-HPLC is an alternative to gel filtration. Also, RP-HPLC is capable of removing molecules from the solution that have molecular weights close to the protein and cannot, therefore, be removed completely by gel filtration. In addition, contaminants such as bacterial endotoxin are also removed effectively by RP-HPLC. Therefore, RP-HPLC may also be used as a final purification step after gel filtration.

Commonly owned U.S. application Ser. No. 946,083 filed Dec. 23, 1986 now abandoned entitled "Purification of Recombinant Beta-Interferon Incorporating RP-HPLC" concerns reverse-phase high performance liquid chromatography (RP-HPLC) methods for purifying recombinant beta-interferon and processes for purifying recombinant beta-interferon incorporating said RP-HPLC methods.

An alternative and preferred procedure is to oxidize selectively, under controlled conditions, the IFN-$\beta$ protein after it has been separated by gel filtration, as described in U.S. Pat. No. 4,572,798 to K. Koths et al. (using an oxidation promoter containing a $Cu^{+2}$ cation) and in U.S. Pat. No. 4,530,787 to Z. Shaked et al. (using o-iodosobenzoic acid), the disclosures of which are incorporated herein by reference. The oxidized product is purified by RP-HPLC or gel filtration followed by RP-HPLC.

It is preferred in carrying out the process of this invention that the last step of purification before stabilization of the formulation is a desalting step employing a transfer component, such as sodium laurate at a pH range of about 8.5 to about 10. The purity of the protein after the chromatography step(s) is at least about 95% and higher, and usually at least about 98%. This highly pure material contains less than about 2 ng endotoxin, usually less than about 0.01 ng endotoxin, per 100,000 units protein bioactivity.

Commonly owned U.S. application Ser. No. 048,686 filed May 11, 1987, now U.S. Pat. No. 4,961,969 concerns a process to obtain purified, biologically active, bacterially produced IFN-$\beta$, wherein the process comprises subjecting reduced, solubilized, bacterially produced IFN-$\beta$ in a chaotropic environment to oxidizing conditions and then removing the chaotropic environment in the presence of an effective amount of a solubilizing additive. Said application is herein incorporated by reference.

The formulation of the protein in accordance with this invention is then carried out as described in detail above. It may be carried out as a separate operation using purified, selectively oxidized protein or in an operation that is integrated with the purification of the selectively oxidized protein. In the latter case, the starting material for the formulation is a protein-containing product from a RP-HPLC treatment of the selectively oxidized product. Preferably a product selectively oxidized by the RP-HPLC product (pool) will comprise a solution of the protein in a water-organic solvent mixture. The nature of the organic solvent will depend upon the solvent system used in RP-HPLC. Examples of systems that may be used are combinations of an organic acid such as acetic acid, trifluoroacetic acid or heptafluorobutyric acid, and an organic solvent such as propanol or acetonitrile.

Further, other conventional solid non-protein bulking/stabilizing agents that are used in pharmaceutical tablet formulation may be used as the carrier. These materials are water soluble, do not react with the IFN-$\beta$ protein, and are themselves stable. They are also preferably non-sensitive to water, that is, non-hygroscopic. Specific examples of such other candidate carriers include starches and starch hydrolysates derived from wheat, corn, rice, and potatoes, as well as micro-crystalline celluloses.

The unit dosage amounts, that is, about 0.125 to 2 mg, preferably 0.25 to 1 mg, of the recombinant beta-interferon in the solution are dispensed into containers, the containers are capped with a slotted stopper, and the contents are lyophilized using conventional freeze-drying conditions and apparatus.

The lyophilized formulations may be reconstituted by injecting into the vial a conventional parenteral aqueous injection such as distilled water for injection, Ringer's solution injection, D5W glucose solution, Hank's solution injection, dextrose injection, dextrose and salt injection, physiological saline injection, or the like, preferably a diluent, more preferably a NaCl solution which yields an isotonic solution upon reconstitution. The injection should be added against the side of the vial to avoid excess foaming. The amount of injection added to the vial will typically be in the range of 1 to 5 ml, preferably 1 to 2 ml.

The reconstituted formulation prepared as described above is suitable for parenteral administration to humans or other mammals in therapeutically effective amounts (i.e., amounts which eliminate or reduce the patient's pathological condition) to provide therapy thereto. IFN-$\beta$ therapy is appropriate for anti-cancer, anti-viral and anti-psoriasis treatment.

The formulations of this invention are useful for parenteral administration, for example, intravenous, intrathecal, subcutaneous, intraperitoneal, intramuscular, intraorbital, opthalmic, intracapsular, intraspinal, intrasternal, topical, intranasal aerosol, scarification, and also, for oral administration. The preferred routes of administration are by intramuscular, subcutaneous and intravenous injection, and by topical administration. The use of non-ionic detergents are especially preferred for topically administered formulations because of their ability to penetrate the skin surface.

The following examples further illustrate the formulations and processes of the invention. These examples are not intended to limit the invention in any manner. In these examples all temperatures are in degrees Celsius unless otherwise indicated.

EXAMPLE 1

An analog IFN-$\beta$ designated IFN-$\beta_{ser17}$ was recovered from *E. coli*. The amino acid sequence of this recombinant IFN-$\beta$ is different from that of native human IFN-$\beta$ in that the cysteine at position 17 has been changed to serine. The strain of IFN-$\beta_{ser17}$-producing *E. coli* (K12/MM294-1) carrying plasmid pSY2501 used in this example was deposited at the American Type Culture Collection on Nov. 18, 1983 under accession number 39,517. Said analog is described in U.S. Pat. Nos. 4,518,584 and 4,588,585 assigned to Cetus Corporation.

The *E. coli* thus transformed were grown in a 1000-liter fermentor at 37° C. The dissolved oxygen was maintained at about 40% by, as necessary: (1) increasing agitation; (2) adding air; and (3) adding oxygen. Once the fermenter was filled with water to the operating volume, the following trace elements were added:

| | |
|---|---|
| ZnSO$_4$.7H$_2$O | 72 mM |
| MnSO$_4$.4H$_2$O | 30 μM |
| CuSO$_4$.5H$_2$O | 3 μM |
| Na$_3$ citrate.2H$_2$O | 1.5 mM |
| KH$_2$PO$_4$ | 21 mM |
| (NH$_4$)$_2$SO$_4$ | 72 mM. |

The fermenter feed and addition vessels were then sterilized according to standard operating procedures. Then the following sterile additions were made:

| | |
|---|---|
| MgSO$_4$.7H$_2$O | 20 mM |
| FeSO$_4$.7H$_2$O | 100 μM |
| L-tryptophan | 70 mg/L |
| thiamine.HCl | 20 mg/L |
| glucose | 5 g/L. |

The fermenter was cooled and inoculated with frozen or seed *E. coli* culture at 2 mg/L. A glucose feed was employed to maintain the glucose concentration between 5-10 g/L. At approximately 15 hours after fermentation was begun, the pH was adjusted with KOH to 6.8. Optical density measurements and residual glucose measurements on samples were taken at 14-16 hours and approximately one hour intervals thereafter.

Induction of IFN-$\beta_{ser17}$ production by depletion of L-tryptophan from the culture medium occurred at about OD$_{680}$=10 followed by the addition of casamino acids to a final concentration of 2% at OD$_{680}$=15. The cultures were harvested when glucose consumption reached 40±6 g/l.

The refractile bodies containing the IFN-$\beta_{ser17}$ protein were then isolated. The harvested material was concentrated about 5-10 fold by circulating the harvest material under pressure through UF cross-flow filtration cartridges with a 100K molecular weight cutoff. Cells were disrupted by 3 passes through a Manton-Gaulin high-pressure homogenizer at 6,000 to 8,000 psig.

EDTA was added to the disruptate to a final concentration of 5 mM. The suspension was then diafiltered against 5 volumes of deionized water.

EDTA was then added to a final concentration of 2 mM. Octanol was added to 1% (v/v) to kill any residual live bacteria in the diafiltered product. The suspension was redisrupted by passing it twice through the Manton-Gaulin high-pressure homogenizer at 6,000-8,000 psig.

Sucrose was added to the redisruptate to a final concentration of 23% (wt/wt), creating a final density gradient between 1.1 and 1.25 g/ml. The mixture was centrifuged at 10,000 to 15,000×g, and the particle pellet or paste was collected. A temperature of at least 20° C. was maintained prior to and during centrifugation.

The particle pellet was then solubilized in phosphate buffered saline with 2% SDS. Solid DTT and EDTA were added to a final concentration of 10 mM and 2 mM, respectively. The suspension was heated to 50±5° C. for 10 minutes under nitrogen. The reaction mixture was then cooled to approximately 25° C., and then the pH of the mixture was adjusted to 7.4.

A volume of 2-butanol equal to the total volume of the suspension was measured. The suspension and organic solution were pumped separately but simultaneously at flow rates of 1.1 to 1.3 liters per minute through a static mixer and then into a continuous centrifuge (Westfalia at approximately 11,770×g) for phase separation. The 2-butanol-rich phase containing the IFN-$\beta_{ser17}$ was collected (Organic Extract).

The 2-butanol extract was mixed with 2.5 volumes of 0.1% SDS in phosphate-buffered saline. Solid DTT was added to a final concentration of 2 mM. The pH of the organic extract/buffer solutions was adjusted to 6.2±0.1 with glacial acetic acid (Acid Precipitate).

The mixture was then centrifuged (Sharples centrifuge at 13,200×g) for approximately 2-6 hours, the supernatant was decanted, and the final pellet was then collected (Final Pellet) containing approximately 81% IFN-$\beta$. The final pellet containing the refractile material was then further purified by downstream processing.

The final pellet was then re-suspended with 2% SDS in 50 mM phosphate buffer and 5 mM EDTA. Solid DTT was added to a final concentration of 20 mM, and the pH was adjusted to 8.5 with NaOH. The suspension was heated to 50+5° C. for 10 minutes under nitrogen, and then cooled to approximately 25° C. The pH was then adjusted to a pH of 5.5 with glacial acetic acid, and the solution was filtered through a 0.65 μm filter.

The filtrate was then processed by pre-column chromatography by loading a Sephacryl ® S200 column and collecting fractions into clean, depyrogenated vessels using an elution buffer that is composed of 50 mM acetate, pH 5.5, 1 mM EDTA and 1% SDS. The fractions containing the IFN-$\beta$ monomer were pooled.

The pre-column pool was then concentrated by using a hollow-fiber ultrafiltration unit with a 10K molecular weight cut-off.

The concentrated pre-column pool was then oxidized using o-iodosobenzoic acid (IBA). The oxidation was effected by adding equimolar amounts of protein and IBA into a reaction vessel containing mM sodium pyrophosphate, 0.1% SDS and 1 mM EDTA. A 20 $\mu$M excess of IBA was present at the end of the oxidation. The pH was controlled at 9.0±0.1 with NaOH during oxidation, and adjusted to 5.5±0.2 with glacial acetic acid when the oxidation was completed.

The IFN-$\beta$ protein was then concentrated using a hollow-fiber ultrafiltration unit with a 10K molecular weight cut-off.

The protein was then loaded onto the main column (Sephacryl ® S200-A), and fractions were collected into clean, depyrogenated vessels using an elution buffer that is composed of 50 mM acetate, pH 5.5, 1 mM EDTA and 0.1% SDS.

A SDS-PAGE was performed on samples from each fraction tube starting from the beginning of the peak to be pooled to the end of the peak. Using the SDS-PAGE results, the fractions containing no high molecular weight contaminants were determined. Those fractions were then pooled.

The main column pool was then concentrated by using a hollow-fiber ultrafiltration unit with a 10K molecular weight cut-off.

The above procedure performed with the main column was repeated on a Sephadex ® G-75 column. Using the SDS-PAGE results, the fractions containing neither low nor high molecular weight contaminants were pooled.

The desalting step was then performed at pH 9.2 wherein 0.1% sodium laurate was used as a transfer component as follows. The pH was adjusted with a appropriate basic agent such as 1 mM NaOH.

A Sephadex ® G-25 column was then equilibrated with 0.1% sodium laurate in 10 mM Tris-HCl, pH 9.2 and loaded with the Sephadex ® G-75 pool containing 0.1% SDS. Using the process chromatogram, the IFN-$\beta_{ser17}$ peak was collected. The pH of the eluate was then lowered quickly with 1.0 N HCl to pH 3.0, which precipitated the sodium laurate, but left the IFN-$\beta_{ser17}$ in solution.

The mixture was centrifuged at 35,000×g for 30 minutes and the supernatant was filtered through a 0.22 micron nitrocellulose filter. SDS concentration was assayed by acridine orange. [Sokoloff et al; "Rapid Spectrophotometric Assay of Dodecyl Sulfate Using Acridine Orange," *Anal. Biochem;* 118:138-141 (1981).] The recovery of the G-25 pool was above 85%, and the SDS concentration was reduced to less than 10 $\mu$g/mg.

The filtered supernatant was then stabilized by adding 0.15% 15 Trycol ® LAL-12. The pH of the formulated product was then raised to about 7.0±0.3 with NaOH. The bulking/stabilizing agent, 5% dextrose, was then added. The solution was then pre-filtered and sterile filtered through 0.45 and 0.22 micron nitrocellulose filters, respectively. Immediately thereafter the correct dosage amounts of the IFN-$\beta_{ser17}$, 0.25 mg containing 0.5×10$^8$ units, were aseptically filled into sterilized vials with sterilized stoppers under sanitary and sterile conditions that were carefully monitored. The vials were then quickly placed in a lyophilizer where appropriate thermocouples were attached. The vials were frozen to between −35° and −45° C. The lyophilization cycle was completed, and the vials were mechanically sealed under a vacuum.

EXAMPLE 2

This example follows procedures similar to those outlined in Example 1 with the main difference being that sodium laurate is employed as the primary solubilizing agent rather than SDS. The other differences are indicated below.

The procedures of this example correspond essentially to those outlined in Schemes 1A and 1B. Therefore, at the point of paste solubilization, instead of 2% SDS, 1-2% sodium laurate in 20 mM disodium phosphate plus a reducing agent (50 mM DTT) is used to solubilize the particle pellet. The pH was adjusted to about 9 with NaOH. Sonication is preferably employed to promote solubilization.

Also, differing from Example 1, is the elimination after the first reduction of the steps of the expanded front-end process, including the Organic extraction, Acid precipitation, Centrifugation, Acid precipitate solubilization, and second Reduction. The buffer is 10 mM Tris.HCl rather than 50 mM acetate for the gel chromatography steps on the Sephacryl ® S200 columns and on the Sephadex ® G-75 column. Further, such gel chromatography is run at pH 9.2 rather than at pH 5.5, as are the Concentration steps.

The elution buffer on the first S200 column contains 1-2% sodium laurate rather than 1% SDS as in Example 1. The elution buffer of the second S200 column contains 0.1-0.5% sodium laurate rather than 0.1% SDS, and the buffer for the G-75 column contains 0.1%-0.5% sodium laurate rather than 0.1% SDS.

During the oxidation step, 1-2% sodium laurate is used rather than 0.1% SDS.

As in Example 1, the IFN-$\beta_{ser17}$ is formulated by lowering the pH of the eluate to about 3, centrifuging and filtering to remove the precipitated sodium laurate, adding an effective amount of one or more biocompatible non-ionic polymeric detergents or a combination of such non-ionic detergents and another solubilizing agent, adjusting the pH to about physiological pH, adding an appropriate bulking/solubilizing agent, preferably dextrose or mannitol, pre- and sterile filtering the pool and immediately lyophilizing the formulated, neutralized product. The primary advantage of the procedures of this example is to arrive at a formulation that is completely or substantially free of SDS.

EXAMPLE 3

The procedure outlined in Example 1 wherein sodium laurate was used as a transfer component on the G-25 desalting column was repeated using a Pharmacia K50 column (1700 ml. bed volume). Fifty ml of the G-75 eluate (approximately 3.64 mg/ml of IFN-$\beta$) was loaded on the K50 column equilibrated in 0.1% sodium laurate in 20 mM sodium phosphate and run at pH 9.2. The recovery of the IFN-$\beta$ was 68%, and the SDS level was less than 10 $\mu$g/mg of protein or less than 1 ppm. At pH 3, the IFN-$\beta$ was soluble with no detergent as shown by UV scan.

EXAMPLE 4

The following IFN-β formulations were prepared according essentially to the procedure of Example 1 where 0.1% sodium laurate was used as a transfer component. No bulking/stabilizing agents, however, were added to the formulations, and they were not lyophilized. Precipitation was checked visually and by UV scan. Table I shows the results.

TABLE I

Durfax ® 80/SDS 0.1%/200 µg/mg
Polysorbate
Remains soluble for days at neutral
pH by UV scan.
Trycol ® LAL(12)/Nopalcol 0.1%/0.05%
POE(12) lauryl ether/PEG(400)
monooleate
Remains soluble for days at pH 7.0 by
UV scan (20 µg/mg SDS).
Triton ® X305/Nopalcol 0.1%/0.05%
$C_8H_{17}$phenyl$(OCH_2CH_2)_{30}OH$/
PEG(400) monooleate
Remains soluble overnight at pH 7.0 for
days at pH 5.0 by UV scan. The
detergent solution without IFN-β is
slightly cloudy (45 µg/mg SDS).
Trycol ® LAL(12) 0.1% POE(12)lauryl ether
Soluble and 6.5 and 6.0. Better UV scan
at 6.0 (10 µg/mg SDS).
Plurafac ® C-17 0.1% modified oxyethylated
straight chain fatty alcohol.
Soluble at pH 6.0 for days (10 µg/mg
SDS)

EXAMPLE 5

Ultracentrifugation Data

Ultracentrifugation is a simple method of detecting the presence of high molecular weight aggregates and oligmers in the formulations of the invention. Ultracentrifugation was performed in a Beckman L8-70 using a type 70.1 Ti rotor. Five milliliter samples of the formulated product, lyophilized and reconstituted, were spun at 55,000 rpm for one hour. The supernatant was measured by absorbance at 20 nm. Said absorbance was then compared tot hat prior to centrifugation. Table II below shows the comparative results of a number of formulations, some of which do not contain biocompatible non-ionic polymeric detergents and are inserted for comparative purposes.

TABLE II

| Samples | Ultracentrifugation 55,000 rpm -- 60 min. | | |
|---|---|---|---|
| | $A_{280}$ Before | $A_{280}$ After | Percent Recovery |
| 1.25% HSA (human serum albumin) | 1.696 | .543 | 32% |
| 0.1% SDS pH 7.5 | .257 | .238 | 93% |
| 0.1% Laurate pH 7.5 | .408 | .392 | 96% |
| 0.1% Durfax ® 80/150 µg/ml SDS pH 7.0 | .306 | .116 | 39% |
| 0.1% Durfax ® 80/200 µg/mg SDS pH 7.0 | .419 | .442 | 105% |
| 0.1% Triton ® X305/0.05% Nopalcol pH 7.0 | .140 | .061 | 46% |
| 0.1% Trycol ®/0.05% Nopalcol pH 7.0 | .357 | .387 | 108% |
| 0.1% Plurafac ® C-17 pH 6.0 | .530 | .456 | 86% |
| 0.1% Trycol ® pH 6.5 | .475 | .415 | 87% |

The results in Table I indicate that the formulations of IFN-β with 0.1% Trycol ® at pH 6.5, 0.1% Plurafac ® C-17 at pH 6.0, 0.1% Trycol ®0.05% Nopalcol ® at pH 7.0, and 0.1% Durfax ® 80/200 µg/mg SDS at pH 7.0 all had significantly less high molecular weight species than the HSA formulation.

EXAMPLE 6

The IFN-β formulations listed in Table I and IFN-β formulations with 0.1% sodium laurate at pH 7.5 and 1.25% normal serum albumin were analyzed by SDS-page electrophoresis under non-reducing conditions. Further, a sample of the purified IFN-β eluate from the G-25 pool that was unformulated was also tested as a control. The sodium laurate, Trycol ® LAL(12)-Nopalcol ®, Plurafac ® C-17, and Trycol ® LAL(12) did not look significantly different from the G-25 pool by SDS-page. There was an extra band present in the Triton ® X305-Nopalcol ® and Durfax ® 80/SDS-page results. However, a Western blot was performed which showed that said band did not stain for IFN-β.

EXAMPLE 7

Dextrose Lyophilized Formulations

The non-ionic detergent formulations listed in Table 1, as well as a 0.1% laurate formulation and a 1.25% human serum albumin formulation, were studied by ultracentrifugation after freeze-drying in 1.25% dextrose. Table III is a compilation of the ultracentrifugation data relating to the dextrose-formulated lyophilized samples. The ultracentrifugation procedure was as that described above in Example 5. Trycol ® LAL(12) at 0.1% concentration and at pH 6.5 did not appear to resolubilize IFN-β after lyophilization. Higher concentrations of Trycol ® LAL(12) were tested, and it was found that a concentration of 0.15% Trycol ® was able to solubilize IFN-β at pH 7.0 with minor aggregation.

Since somewhat lower pH values can be tolerated clinically, Trycol ® LAL(12) and Plurafac ® C-17 were tested at pH 5.0 to see if lower levels of surfactants would solubilize IFN-β at this pH. UV scans show that both detergents were able to solubilize IFN-β at pH 5.0, at concentrations as low as 0.01%.

TABLE III

| Dextrose Lyophilized Formulations | | | |
|---|---|---|---|
| Sample | $A_{280}$ Before | $A_{280}$ After | % Recovery |
| Laurate | 1.023 | 0.485 | 47 |
| Triton ® X305/Nopalcol | 1.325 | 0.960 | 72 |
| Trycol ® LAL(12)/Nopalcol | 0.628 | 0.463 | 74 |
| Durfax ® 80/SDS | 0.688 | 0.289 | 42 |
| Trycol ® LAL(12) (0.1% pH 6.5) | 1.210 | 0.245 | 20 |
| Plurafac ® C-17 (pH 6.0) | 0.561 | 0.394 | 70 |
| HSA Formulation | 1.469 | 0.814 | 55 |
| Starting pH 3.0 | 0.329 | 0.244 | 75 |

EXAMPLE 8

Recombinant IFN-β in formulations with 0.15% Trycol ® at pH 7.0 were tried with other bulking/stabilizing agents (non-reducing sugars) according to the formulation procedure of Example 1. However, in some cases, the formulations were not frozen, some were frozen, and some were frozen slowly. Ultracentrifugation was performed on such samples according to the procedure of Example 5. The test results are included as Table IV below. The results indicated that the different sugars had no effect on the solubility of IFN-β. However, the method of freezing the samples affected whether aggregates were formed. Freezing the samples quickly in dry ice and ethanol did not produce aggregates, while freezing slowing by placing the room-temperature samples in −20° C. caused some degree of aggregation.

TABLE IV

Ultracentrifugation
IFN-β in 0.15% Trycol ®, pH 7.0, With Various Sugars at 5%

| Samples | Treatment | $A_{280}$ Before | $A_{280}$ After | % Recovery |
|---|---|---|---|---|
| 1 H₂O (no bulking agent) | None | 0.400 | 0.367 | 91.8 |
| 2 Mannitol | None | 0.400 | 0.370 | 92.5 |
| 3 Sorbitol | None | 0.409 | 0.378 | 92.4 |
| 4 Dextrose | None | 0.496 | 0.484 | 97.6 |
| 5 Inositol | None | 0.403 | 0.351 | 87.1 |
| 6 H₂O | Frozen | 0.388 | 0.384 | 99.0 |
| 7 Mannitol | Frozen | 0.412 | 0.379 | 92.0 |
| 8 Sorbitol | Frozen | 0.404 | 0.384 | 95.1 |
| 9 Dextrose | Frozen | 0.601 | 0.579 | 96.3 |
| 10 Inositol | Frozen | 0.397 | 0.375 | 94.5 |
| 11 Dextrose | Frozen Slowly | 0.656 | 0.584 | 89.0 |
| 12 Mannitol | Frozen Slowly | 0.296 | 0.249 | 84.1 |

EXAMPLE 9

Linear Non-Isothermal Stability Studies

Although linear, non-isothermal stability studies (LNS) cannot predict the absolute long-term stability of a given formulation, they are a useful tool in comparing the relative stability of different formulations and can be performed in a matter of days. Samples were prepared for the stability studies by chromatography on a G-25 desalting column using 0.1% sodium laurate as a transfer component, as described in Example 1. All the formulations tested for the LNS studies included 5% mannitol and were lyophilized. Final container vials were kept at 4° C. until submitted for study. The linear non-isothermal stability (LNS) studies were performed running a linear temperature ramp from 50° C. to 90° C. at 1.5° C. rise/hour. Bioactivity was measured by a yield reduction assay as described in Steward and Lockhart, J. of Virol; 6:795-799 (1970).

At pre-set intervals, 0.5 ml was removed from each vial with sterile, plastic syringes, transferred to plastic assay tubes, and frozen at −20° C. until assayed. The intervals were approximately 24 hours apart. The samples were thawed, randomized, and then submitted for yield reduction assay on either day 1, day 2, or day 3.

FIG. 1 shows LNS study results for normal, high and low dose human serum albumin formulations of IFN-β as well as 1% sodium laurate formulations of IFN-β. The graph of FIG. 1 indicates that the high dose HSA formulation is relatively more stable than the normal dose HSA formulation, which is, in turn, more stable than the low dose HSA and laurate formulations.

Figure 2:
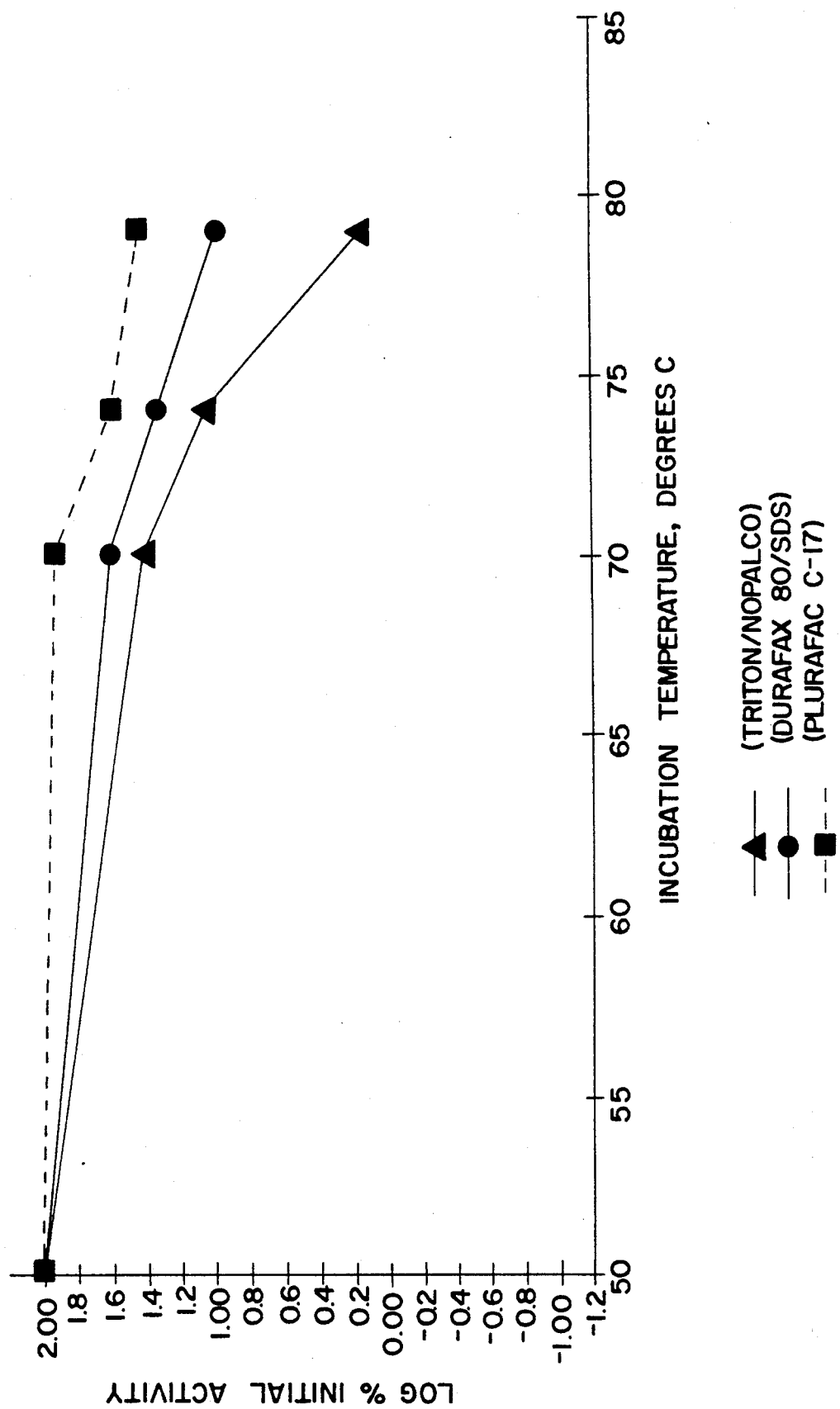

FIG. 2 compares the relative stability of three mannitol formulations of the instant invention. The scale is the same as that for FIG. 1. From a comparison of FIGS. 1 and 2, one would predict that the Triton X305/Nopalcol formulation is as stable as the normal dose HSA formulated IFN-β, and that Plurafac ® C-17 formulation is as stable as the high dose HSA formulated IFN-β.

Figure 3:
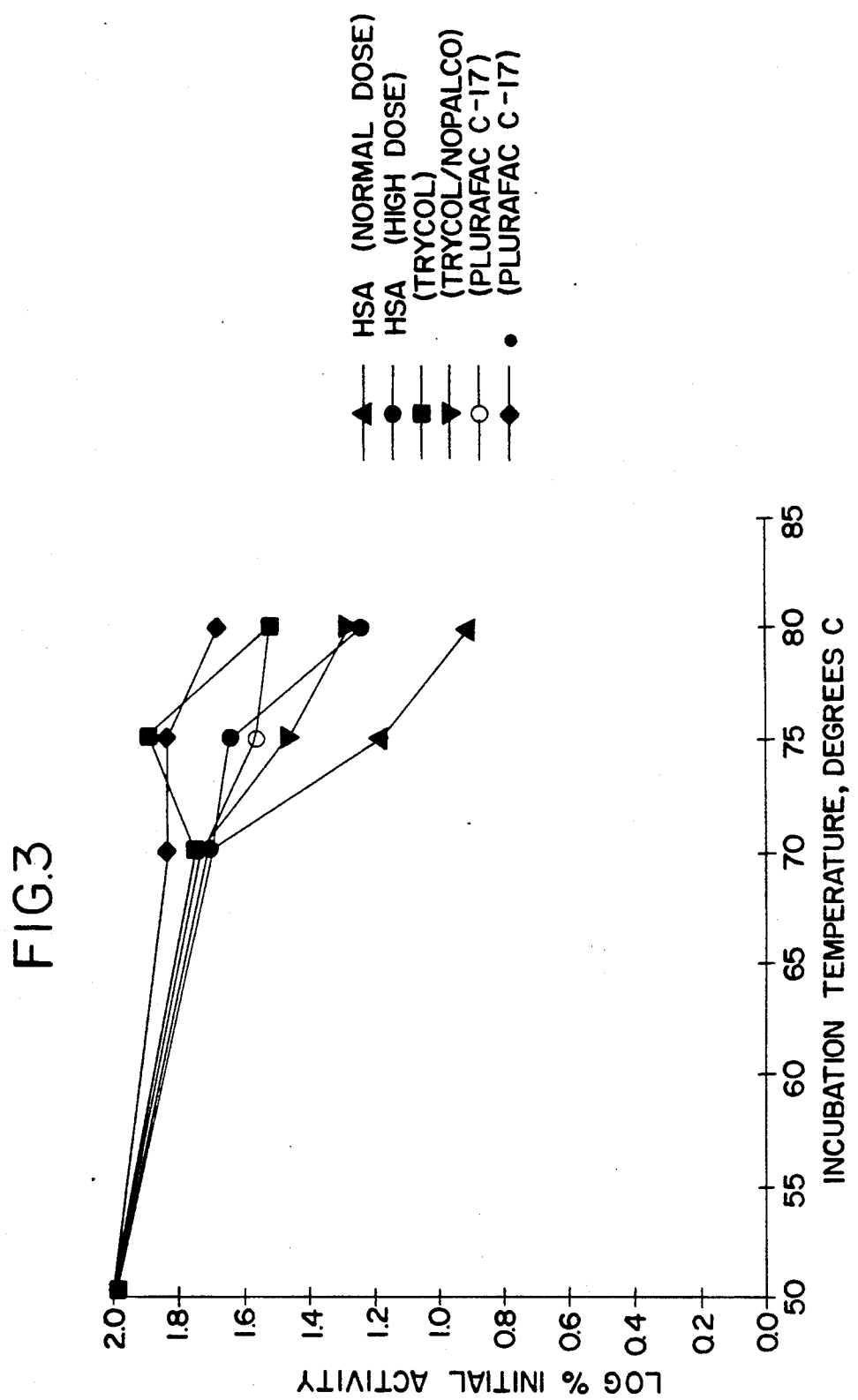
Figure 4:
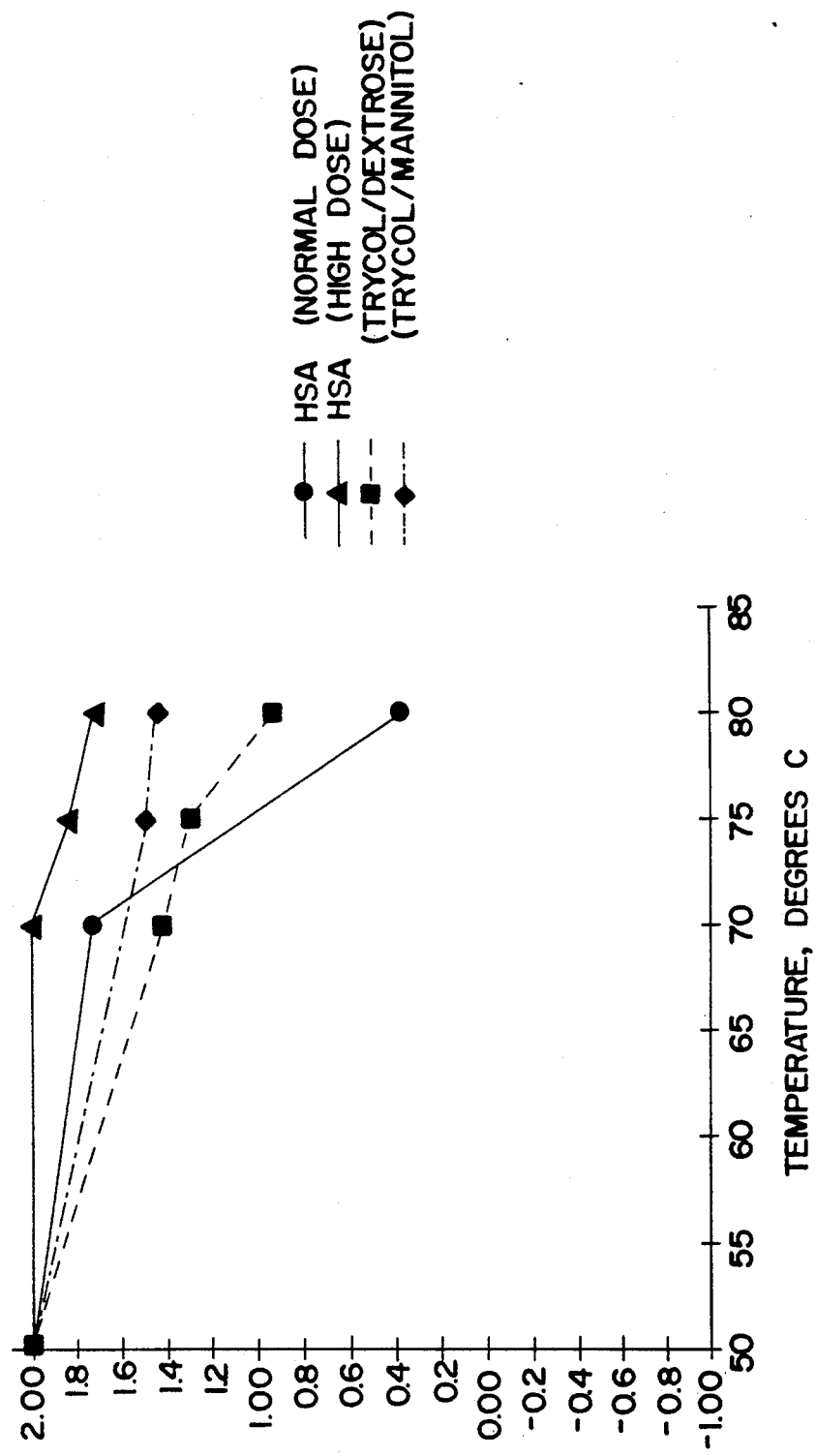

FIG. 3 illustrates the relative stability of normal and high dose HSA formulated β-IFN and 0.25 mg/ml IFN-β in 5% mannitol with 0.1% Plurafac ® C-17 at pH 6.0 as well as a 0.01% Plurafac ® C-17 formulation at pH 5 as represented by the diamonds on FIG. 3. The results show that the 0.1% Plurafac ® C-17 formulation is at least as stable as the high-dose human serum albumin formulation. Further, the LNS study predicts that the 0.01% Plurafac ® C-17 formulation at pH 5 will also have good long-term stability. The Trycol ® LAL(12) at 0.15% formulation at pH 7 is predicted from the LNS study to be as stable as the high-dose HSA formulation, whereas the Trycol ® LAL(12)-Nopalcol formulation should be more stable than the HSA normal dose formulation.

EXAMPLE 10

Toxicity Studies

IFN-β was purified as described in Example 1 wherein SDS was removed from the G-75 pool by desalting on a G-25 column run in 0.1% sodium laurate as a transfer component. Formulation with representative formulants of the invention was performed as described.

For these toxicity studies, 8 mice (4 female and 4 male) were tested per formulation. The representative formulations tested each contained one of the solubilizer/stabilizer compositions listed in Table I, supra, 5% mannitol and 0.25 mg/ml of IFN-β. All the formulations were lyophilized and reconstituted in sterile water. Each animal was injected with 0.2 ml intravenously via a lateral tail vein. Additionally, four mice (2 female and 2 male) were injected with 0.2 ml of excipient containing 1.0% detergent. These toxicity studies resulted in no deaths and no weight change of the tested mice. Such data confirm the oral toxicology reports submitted to applicants by the manufacturers of representative non-ionic surfactants used in the formulations of the invention as noted above in the summary of the invention.

EXAMPLE 11

Timing of Formulation Steps

The formulation step was performed the day after the desalting step employing sodium laurate as a transfer component on a G-25 column (see Example 1) was run and the sodium laurate was removed. The non-formulated IFN-β was kept at pH 3 and at 4 degrees centigrade overnight before formulation. Those formulations were compared to formulations made immediately after running the G-25 column. Results indicate that running the G-25 desalting column 24 hours before the formulation does not increase the level of aggregates. When the G-25 column was run the day before, and IFN-β kept refrigerated overnight at pH 3.0, and the formulations were neutralized to pH 7 four hours before lyophilization, a 30% to 40% increase in the amount of aggregation was obtained when compared to samples that were neutralized immediately before lyophilization. The results below in Table V indicate that lyophilization timing for representative formulations of the invention is critical to the level of aggregation. Lyophilization, immediately after neutralization of the IFN-β protein solution, results in very low levels of aggregates.

TABLE V

| | LYOPHILIZATION TIMING | |
|---|---|---|
| | 4 HRS. | IMMEDIATELY |
| TRITON X305/NOPALCOL | 58% | 92% |
| PLURAFAC C-17 | 50% | 85% |

EXAMPLE 12

Mannitol Versus Dextrose Formulations

Table VI shows the results of ultracentrifugation studies on mannitol, 2.5% mannitol and 5% dextrose formulations, respectively, wherein Trycol ® 0.15% at pH 7 is the stabilizer/solubilizer. Ultracentrifugation data of such formulations prepared according to Example I indicate that mannitol in some way appears to interfere with the solubility of IFN-$\beta$. Therefore, dextrose alone is considered to be a more preferred bulking/stabilizing agent than mannitol alone for the formulations of this invention.

TABLE VI

Ultracentrifugation Mannitol vs. Dextrose

| | Trycol ® 0.15% pH 7.0 |
|---|---|
| 5% Mannitol | 79.5% |
| 2.5% Mannitol | 84.5% |
| 5% Dextrose | 90.5% |

EXAMPLE 13

LNS Studies of Dextrose- and Mannitol-Containing Formulations

LNS studies were performed on representative formulations of the instant invention to compare dextrose versus mannitol as the bulking/stabilizing agent therein. Trycol ® LAL(12) IFN-$\beta$ compositions prepared as according to Example 1 were formulated with 5% dextrose and 5% mannitol, respectively. The LNS results are presented in FIG. 6. A comparison with a normal and high dose HSA formulated IFN-$\beta$ formulation indicate that the non-ionic surfactant containing formulations of the invention are predicted to be at least as stable as the normal dose HSA IFN-$\beta$ formulation. No difference in stability was observed between the mannitol- and dextrose-formulated compositions.

EXAMPLE 14

This example shows the results of a representative screening process of this invention for candidate formulating agents. G-75 purified IFN-$\beta$ was eluted from a G-25 Sephadex column equilibrated in laurate buffer (phosphate) at pH 9.2. The sodium laurate was precipitated at pH 3 as described in Example 1. The soluble IFN-$\beta$ was separated by centrifugation and added at pH 3 to the non-detergent stabilizer, glycerol, at a concentration by volume of 25%, and a non-ionic detergent, as indicated in Table VII below, at a concentration of 0.01%. The pH of the solutions was then raised to 5. The chromatography was performed at room temperature. After the formulations were made, they were observed for any formation of a precipitate; the observations were recorded; and then the samples were kept at 4° C. for 24 hours to several weeks.

All samples were centrifuged according to the procedures of Example 5, and the amount of IFN-$\beta$ remaining in solution was calculated based on $A_{280}$. Aliquots for bioassay [by the cytopathic effect assay described by Steward, The Interferon System, p 17 (1981)] were taken at time=0, 24 hours, 48 hours and one week.

The results of such experiments are shown in Tables VII and VIII. Table VII indicates that 96-100% of IFN-$\beta$ formulated with 25% glycerol and 0.01% of the specified non-ionic detergent remains soluble. Table VIII shows the bioassay results for such samples. After formulation, all the samples maintained bioactivity over the course of one week at 4° C.

TABLE VII

Recovery of Protein in the Supernatant for Various Formulations

All Samples in 25% Glycerol and 25 mM sodium phosphate

| Formulation | Precipitation at 5 Minutes | % Recovery by $A_{280}$ (24 Hours) | % Recovery by $A_{280}$ (1 Week) |
|---|---|---|---|
| 0.01% Trycol LAL-12, pH 5 | 0 | 100 | 96 |
| 0.01% Tween 80, pH 5 | 0 | 100 | 105 |
| 0.01% Pluronic F-68, pH 5 | 0 | 97 | 102 |

TABLE VIII

Specific Activity (CPE Assay) of Various Formulations ($U/mg \times 10^7$)

| Sample | 0 Hours | 24 Hours | 48 Hours | 1 Week |
|---|---|---|---|---|
| 25% Glycerol, 0.01% Trycol, pH 5 | 3.0 | 0.5 | 0.3 | 0.9 |
| 25% Glycerol, 0.01% Tween 80, pH 5 | 10.0 | 10.5 | 7.4 | 4.5 |
| 25% Glycerol, 0.01% Pluronic F-68, pH 5 | 10.0 | 9.7 | 9.7 | 4.1 |

EXAMPLE 15

The example illustrates a number of different combinations of bulking/stabilizing agents for lyophilized formulations of IFN-$\beta$. The IFN-$\beta$ used for this example was extracted and purified essentially according to Example 1, up to and including the point at which the IFN-$\beta$ filtrate was stabilized by the addition of 0.15% Trycol ® LAL-12. Then, 5% dextrose (wt./vol.) was added to a 10 ml aliquot of the IFN-$\beta$ stabilized filtrate, and the following combinations of bulking/stabilizing agents were similarly each added respectively to 10 ml aliquots of the IFN-$\beta$ filtrate (all percentages are weight to volume concentration ratios): 0.1% dextrose/2% mannitol; 0.2% dextrose/2% mannitol; and 0.1% dextrose/2% glycine. The pH of each 10-ml ml aliquot was then raised to about 6.0 with NaOH. The solutions were then pre-filtered and sterile filtered through 0.45 and 0.22 micron nitrocellulose filters, respectively. Then, the correct dosage amounts of the IFN-$\beta_{ser17}$ (0.25 mg/ml) were aseptically filled into sterilized vials with sterilized stoppers under sanitary and sterile conditions that were carefully monitored.

The vials were then placed in a lyophilizer where appropriate thermocouples were attached. The lyophilization cycle proceeded as follows: the temperature was lowered to −30° C. at which temperature the vials were held for primary drying (under vacuum) for approximately 12 hours; and a two-stage ramp was performed wherein the first stage was a 3° C./hour rise in temperature to 5° C. at which temperature the vials were held for 12 hours, and wherein the second stage was a 3° C./hour rise in temperature to 15° C. at which temperature the vials were held for 24 hours. The vials were then refrigerated at 2° to 8° C. until they were reconstituted with water for injection, added in a 1/1 ratio (vol./vol.) and tested by ultracentrifugation and UV scanning as described in Example 5, above. The ultracentrifugation results are listed below in Table IX.

TABLE IX

| IFN-β Formulated with Trycol ® LAL-12 and Various Bulking/Stabilizing Agents | |
|---|---|
| Bulking/Stabilizing Reagents % (wt/vol.) | Ultracentrifugation Recovery (%) |
| 5% Dextrose | 95% |
| 0.1% Dextrose/2% Mannitol | 88% |
| 0.2% Dextrose/2% Mannitol | 89% |
| 0.1% Dextrose/2% Glycine | 76% |

The plug appearance for each formulation was good. If a standard lyophilization procedure were performed, for example, a primary drying period at −30° C. for 12 hours followed by a 12° C./hour ramp to 15° C., the plug for the 5% dextrose containing formulation appears somewhat collapsed, although the ultracentrifugation recovery and UV scan results are equivalent to that achieved with the above-described slow, two-stage ramp lyophilization protocol. However, the plug appearance for the formulations, other than those containing 5% dextrose as the bulking stabilizing agent, lyophilized according to a standard protocol is the same as for that when a two-stage ramping protocol is employed.

The UV scanning results showed very little aggregation for the formulations containing 5% dextrose, 0.1% dextrose/2% mannitol, and 0.2% dextrose/2% mannitol, as bulking/stabilizing agents; however, more aggregation was seen in the formulation containing 0.1% dextrose/2% glycine as the bulking/stabilizing agent, making it a less preferred bulking/stabilizing agent combination than the others tested.

CONCLUSION

In summary, it can be seen that the IFN-β formulations of the present invention containing biocompatible non-ionic polymeric detergents screened according to the processes of the instant invention and a bulking/stabilizing agent are desirable pharmaceutical compositions. Said IFN-β formulations are at least as stable as HSA formulations, and do not contain significant amounts of aggregates. Improved formulation processes are also described herein which result in formulations having very low levels of aggregates and other potentially immunogenic characteristics and minimal or no amounts of strong solubilizing agents, such as SDS. The formulations of this invention are further non-toxic and have good shelf life.

DEPOSITS

As mentioned above, a culture of *E. coli* K12/MM294-1 carrying plasmid pSY2501 was deposited at the American Type Culture Collection 12301 Parklawn Drive, Rockville, Md. 20852, U.S., on Nov. 8, 1983 under ATCC No. 39,517.

Said deposit was made pursuant to a contract between the ATCC and the assignee of this patent application, Cetus Corporation. The contract with the ATCC provides for permanent availability of said strain and progeny thereof to the public upon issuance of a U.S. patent related to this application describing and identifying the deposit or upon the publication or laying open to the public of any U.S. or foreign patent application, whichever comes first, and for the availability of the strain and the progeny thereof to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the strain on deposit should die or be lost or destroyed when cultivated under suitable conditions, it will be promptly replaced upon notification with a viable culture of the same strain.

The deposit agreement under terms of the Budapest Treaty assures that said culture deposited will be maintained in a viable and uncontaminated condition for a period of at least five years after the most recent request for the furnishing of a sample of the deposited microorganism was received by the ATCC and, in any case, for a period of at least 30 years after the date of the deposit.

The culture was made available on May 21, 1985. Availability of the deposited strain is not to be construed as a license to practice the invention in contravention of the rights granted under the authority of any government in accordance with its patent laws.

Also, the present invention is not to be considered limited in scope by the strain deposited, since the deposited embodiments are intended only to be illustrative of particular aspects of the invention. Any microorganism strain which is functionally equivalent to that deposited is considered to be within the scope of this invention. Further, various modifications of the invention in addition to those shown and described herein apparent to those skilled in the art from the preceding description are considered to fall within the scope of the appended claims.

What is claimed is:

1. A method of screening for one or more biocompatible non-ionic polymeric detergents or for combinations of one or more of said detergents with another solubilizing or stabilizing agent capable of solubilizing and stabilizing pharmaceutical compositions of recombinant interferon-β (IFN-β), comprising the steps of:
    (a) passing extracted, purified IFN-β in sodium dodecyl sulfate (SDS) on a desalting column equilibrated in sodium laurate in an elution buffer at pH 9.0–10.0 to form an eluate;
    (b) lowering the pH of the eluate to about pH 2–3.3;
    (c) centrifuging and filtering the eluate to remove the precipitated sodium laurate;
    (d) adding to the filtrate an effective amount of one or more of said detergents or said combination of one or more of said detergents with another solubilizing or stabilizing agent;
    (e) adjusting the pH of the filtrate to 3.5 to 9.5; and
    (f) allowing said filtrate to stand for about 24 hours at pH 3.5 to 9.5.

2. A method according to claim 1 wherein said other solubilizing or stabilizing agent is glycerol at a concentration (v/v) range of from about 5% to about 50%.

3. A method of preparing stable, pharmaceutical compositions of recombinant interferon-β (IFN-β) protein comprising the steps of:
    (a) extracting the IFN-β from the disruptate of a host organism transformed to produce the protein;
    (b) purifying the IFN-β using as the last purification step a desalting step at a pH range of about 8.5 to 10 employing an elution buffer containing a fatty acid salt having a carbon chain containing from about 10 to about 12 carbons to form a desalted pool;
    (c) lowering the pH of the desalted pool to a pH of about 2 to 4 thereby precipitating the fatty acid salt;
    (d) removing the precipitated salt from the pool by centrifugation and filtration;

(e) adding to the desalted pool an effective amount of one or more non-ionic biocompatible polymeric detergents, or a combination of one or more biocompatible non-ionic polymeric detergents and another solubilizing or stabilizing agent, in effective amounts to stabilize and solubilize the IFN-$\beta$;

(f) adjusting the pH of the pool to a range of between 4.0 and 8.0;

(g) adding an effective amount of a bulking/stabilizing agent to the pool; and (h) lyophilizing the formulation.

4. A method of preparing stable, pharmaceutical compositions of recombinant interferon-$\beta$ (IFN-$\beta$) protein comprising the steps of:

(a) isolating refractile bodies containing the IFN-$\beta$ from a host organism transformed to produce said IFN-$\beta$;

(b) solubilizing said refractile bodies by employing sodium laurate;

(c) extracting and purifying said IFN-$\beta$ from the solubilized refractile material employing sodium laurate as the primary solubilizing agent;

(d) lowering the pH of the purified IFN-$\beta$ to a pH from about 2 to about 4;

(e) centrifuging and filtering the purified IFN-$\beta$ solution to remove the sodium laurate precipitate to create an IFN-$\beta$ pool;

(f) desalting the IFN-$\beta$ pool at a pH from about 2 to 4;

(g) adding to the IFN-$\beta$ protein solution an effective amount of one or more non-ionic biocompatible polymeric detergents, or of a combination of a non-ionic biocompatible polymeric detergent and another solubilizing or stabilizing agent to stabilize and solubilize the IFN-$\beta$;

(h) adjusting the pH of the IFN-$\beta$ solution to a pH range of 3.5 to 9.5;

(i) adding to the solution an effective amount of a bulking/stabilizing agent; and (j) lyophilizing the formulation.

5. A method of extracting recombinant interferon-$\beta$ (IFN-$\beta$) from a bacterial host transformed to produce it and then purifying and formulating said IFN-$\beta$ comprising the steps of:

(a) growing the transformed bacterial hosts in an appropriate fermentation medium;

(b) concentrating the bacterial host in the fermentation medium;

(c) disrupting the cell wall and cell membrane of the bacterial host;

(d) removing greater than 99% by weight of the salts from said disruptate by diafiltration or centrifugation;

(e) redisrupting the desalted disruptate;

(f) adding a material to the disruptate to increase the density or viscosity of, or to create a density or viscosity gradient in, the liquid within the disruptate;

(g) separating the refractile material from the cellular debris by high-speed centrifugation;

(h) solubilizing the refractile material in an aqueous buffer containing a reducing agent;

(i) extracting the solubilized refractile material with 2-butanol or 2-methyl-2-butanol;

(j) isolating said refractile material from the extractant;

(k) solubilizing the resulting refractile material, which contains IFN-$\beta$, with an aqueous solution of sodium dodecyl sulfate at an IFN-$\beta$ to sodium dodecyl sulfate ratio of about 1:3 to form a solution;

(l) adjusting the pH of the solution to about 9.5 and reducing the solubilized IFN-$\beta$ with dithiothreitol;

(m) purifying the reduced IFN-$\beta$ by chromatography;

(n) oxidizing the IFN-$\beta$ from step (m);

(o) further purifying the oxidized IFN-$\beta$ by gel chromatography and collecting the eluate containing the purified IFN-$\beta$;

(p) desalting the purified IFN-$\beta$ eluate in a desalting column equilibrated and run in sodium laurate at pH 9.0 to 9.8;

(q) lowering the pH of the eluate to pH 3.0;

(r) centrifuging and filtering the solution to remove the precipitate;

(s) adding to the filtrate an effective amount of one or more non-ionic biocompatible polymeric detergents or a combination of one or more of said detergents and another solubilizing or stabilizing agent, to solubilize and stabilize the IFN-$\beta$;

(t) adjusting the pH of the solution to 4.0 to 9.5;

(u) adding an appropriate bulking/stabilizing agent in a concentration of from about 0.25% to about 10%; and (v) lyophilizing the IFN-$\beta$ solution.

6. A method according to claim 5 wherein the bulking/stabilizing agent of step (u) is dextrose and wherein the lyophilizing of step (v) is performed by a procedure incorporating a two-stage ramp.

7. A method according to claim 6 wherein the lyophilization procedure comprises the steps of:

(a) freezing the IFN-$\beta$ solution for from about 2 to about 6 hours at a temperature range from about $-70°$ C. to about $-20°$ C.;

(b) lyophilizing the frozen IFN-$\beta$ solution of step (a) for from about 12 to about 48 hours;

(c) ramping at a rate of from about $3°$ C./hour to about $12°$ C./hour to a temperature range from about $-5°$ C. to about $+10°$ C.;

(d) holding at the temperature range of step (c) for from about 6 to about 18 hours;

(e) ramping for from about $3°$ C./hour to about $12°$ C./hour to a temperature range of about $+10°$ C. to about $+25°$ C.; and (f) holding at the temperature range of step (e) for at least 12 hours.

* * * * *